US006423073B2

(12) United States Patent
Bowman

(10) Patent No.: US 6,423,073 B2
(45) Date of Patent: Jul. 23, 2002

(54) INSTRUMENT FOR INSERTING GRAFT FIXATION DEVICE

(75) Inventor: Steven M. Bowman, Sherborn, MA (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 09/793,216

(22) Filed: Feb. 26, 2001

Related U.S. Application Data

(63) Continuation-in-part of application No. 09/535,189, filed on Mar. 27, 2000, which is a continuation-in-part of application No. 09/360,367, filed on Jul. 23, 1999, now Pat. No. 6,179,840.

(51) Int. Cl.⁷ .............................................. A61B 17/58
(52) U.S. Cl. .................... 606/104; 606/184; 606/88; 606/100
(58) Field of Search ..................... 606/104, 59, 54, 606/53, 56, 72, 75, 96, 97, 98, 99, 100, 88, 86, 184; 623/20.11

(56) References Cited

U.S. PATENT DOCUMENTS

| 4,438,769 A | 3/1984 | Pratt et al. |
| 4,454,875 A | 6/1984 | Pratt et al. |
| 4,548,202 A | 10/1985 | Duncan |
| 4,884,572 A | 12/1989 | Bays et al. |
| 5,059,206 A | 10/1991 | Winters |
| 5,269,783 A | 12/1993 | Sander |
| 5,352,229 A | 10/1994 | Goble et al. |
| 5,454,814 A | 10/1995 | Comte |
| 5,500,000 A | 3/1996 | Feagin et al. |
| 5,520,700 A | 5/1996 | Beyar et al. |
| 5,534,006 A * | 7/1996 | Szabo et al. ................ 606/100 |
| 5,569,252 A | 10/1996 | Justin et al. |
| 5,643,319 A | 7/1997 | Green et al. |
| 5,647,874 A | 7/1997 | Hayhurst |
| 5,656,492 A | 8/1997 | Glowacki et al. |
| 5,658,313 A | 8/1997 | Thal |
| 5,688,284 A * | 11/1997 | Chervitz et al. ............... 606/96 |
| 5,690,636 A * | 11/1997 | Wildgoose et al. ......... 606/184 |
| 5,702,462 A | 12/1997 | Oberlander |
| 5,788,701 A * | 8/1998 | McCue .......................... 606/88 |
| 6,022,352 A | 2/2000 | Vandewalle |
| 6,083,225 A * | 7/2000 | Winlow et al. ............... 606/99 |
| 6,187,009 B1 | 2/2001 | Herzog et al. |
| 6,254,606 B1 * | 7/2001 | Carney et al. ................ 606/98 |

FOREIGN PATENT DOCUMENTS

| EP | 0 589 306 | 3/1994 |
| EP | 0 770 354 | 5/1997 |
| EP | 0578425 | 9/1997 |
| WO | 0 390 613 | 10/1990 |
| WO | WO 99/52478 | 10/1999 |

OTHER PUBLICATIONS

Bonding of Cartilage Matrices with Cultured Chondrocytes: An experimental Model; GUISEPPE M. PERETTI; MARK A. RANDOLPH, ENZO M. CARUSO; FRANCESCO ROSSETTI; AND DAVID J. ZALESKE.

* cited by examiner

Primary Examiner—Pedro Philogene

(57) ABSTRACT

An instrument for inserting a graft fixation device. The fixation device is useful for affixing a tissue graft to a bone or other body surface. The graft fixation device comprises two implantation members connected by a connecting member. The fixation device can be combined with insertion members. The implantation members have longitudinal passageways therethrough. The instrument has a hammer handle slidably mounted to a slide rod. The slide rod is mounted at an angle to a mounting member. A mounting rod having an angulated distal end is mounted to the mounting member. Prongs extend longitudinally out from the angulated distal end. The longitudinal axis of the slide rod is parallel to the longitudinal axis of the angulated distal end. The prongs are optionally removably mounted in an end housing mounted to the angulated distal end.

6 Claims, 29 Drawing Sheets

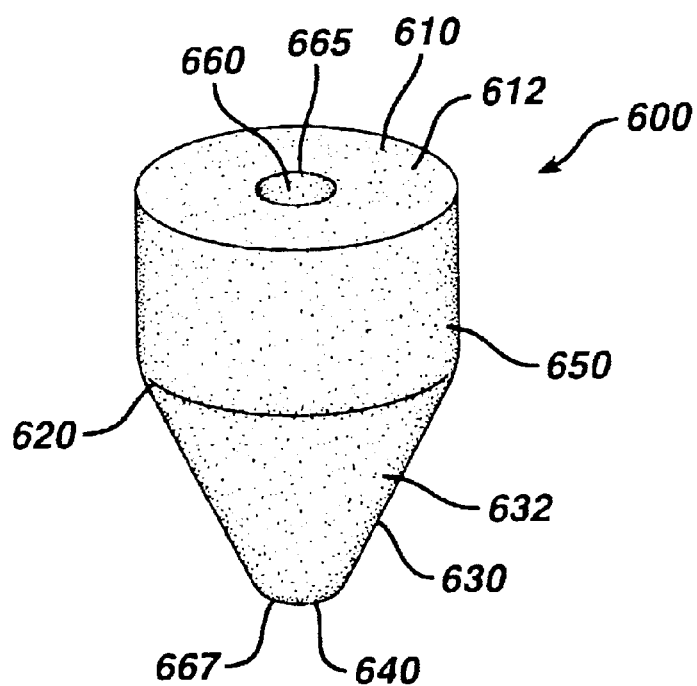
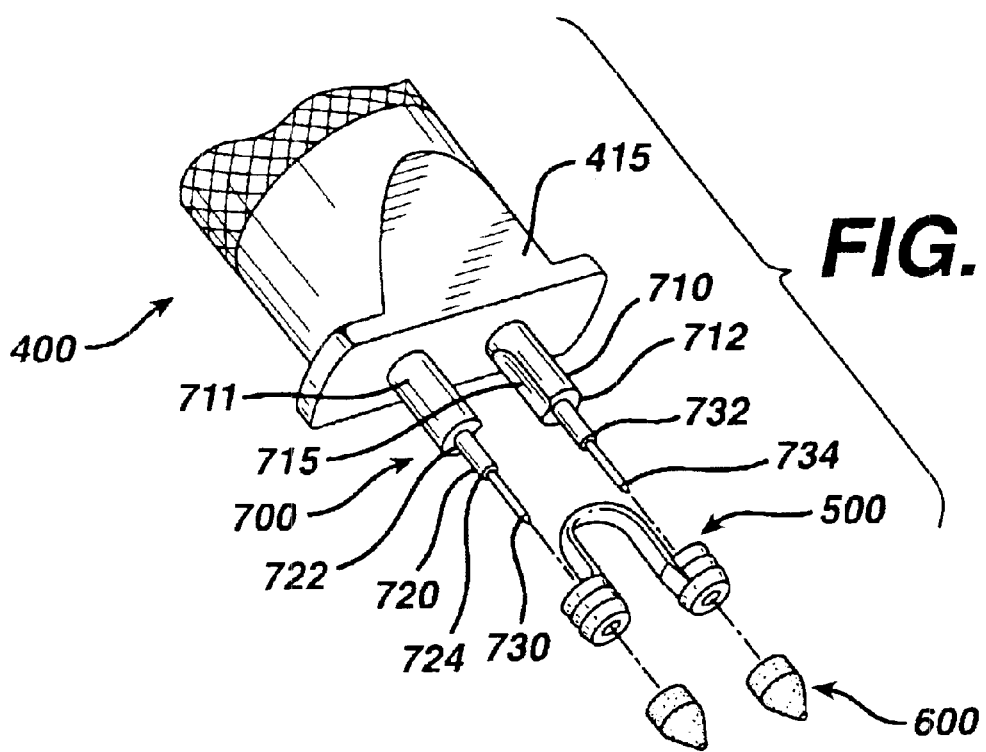

INSTRUMENT FOR INSERTING GRAFT FIXATION DEVICE

This is a continuation-in-part application of commonly assigned U.S. patent application Ser. No. 09/535,189 filed on Mar. 27, 2000 which is a continuation-in-part application of U.S. patent application Ser. No. 09/360,367 filed on Jul. 23, 1999, now U.S. Pat. No. 6,179,840 which are incorporated by reference.

TECHNICAL FIELD

The field of art to which this invention relates is surgical fastening devices, in particular, surgical fastening devices for fixating tissue grafts to bone.

BACKGROUND OF THE INVENTION

The medical technology associated with tissue engineering has advanced at a rapid pace. In particular, it is now known to harvest cells from the human body, for example, chondrocytes and fibrochrondrocytes from the knee joint. These autologous cells are then cultured in a laboratory environment on a bioabsorbable matrix. The matrix will typically have a shape substantially similar to the tissue section which needs to be replaced. After a sufficient period of time in an appropriate culture medium at the proper environmental conditions, the harvested cells will grow on the matrix to form an implantable section of tissue having substantially the same physical configuration as the section of tissue which needs to be replaced in the patient. Such a tissue-engineered construct, consisting of cells on the matrix (or, alternatively, consisting of a matrix alone without cells), is then affixed to the bone site using conventionally known surgical fasteners including sutures, periosteal coverings, or fibrin glue.

The advantages of tissue engineering are many, not the least of which is, for example, that it is now possible to replace cartilage with living cartilage tissue. In addition, the likelihood of rejection of the tissue implant is minimized since the cartilage tissue which has been grown in-vitro is identical to the autologous cartilage of the patient.

Although existing matrix fixation devices are adequate for their intended use, there are also some disadvantages attendant with their use. First of all these fixation devices are generic in the sense that they are not specifically designed for matrix fixation to bone or soft tissue, but can be used for a variety of surgical procedures. Other disadvantages include the difficulty in using many of these devices in a minimally invasive arthroscopic procedure. Additional disadvantages include the difficulty and surgical challenge of harvesting a piece of periosteum for use as a periosteal flap, the significant patient morbidity associated with such harvesting, and the difficulty in suturing such a thin, compliant material to surrounding tissue.

Accordingly, there is a need in this art for novel fixation devices that will effectively affix a matrix of tissue-engineered tissue to a bone or other anchoring site so that the tissue may continue to grow and regenerate in the patient's body.

DISCLOSURE OF THE INVENTION

Therefore, it is an object of the present invention to provide a fixation device that effectively fixates a tissue-engineered matrix to a bone or other anchoring site, thereby enabling the implanted matrix to remain in place while the tissue continues to grow and regenerate.

It is a further object of the present invention to provide such a device for fixating a matrix to a bone site which is easily installed using an arthroscopic procedure or an open procedure.

It is yet a further object of the present invention to provide such a device for fixating a matrix to a bone site which does not require sutures or suture knot tying.

It is still yet a further object of the present invention to provide a surgical method for fixating a matrix utilizing such a device in a location within a patient's body.

Accordingly, a graft fixation device is disclosed. The graft fixation device has first and second implantation members. The members are elongated and preferably have a cylindrical configuration. The members also have distal ends, proximal ends, and longitudinal axes. There are longitudinal passages extending through the entire length of each implantation member. The members have outer surfaces. The implantation members are connected to each other by a rod member having first and second ends and a central section. The first end of the rod member extends from the proximal end of the first implantation member and the second end of the rod member extends from the proximal end of the second implantation member. The rod member is preferably relatively rigid and may be configured to have a variety of geometric shapes, for example, an inverted "U" shape. However, the rod member may also be flexible. The rod member maintains the implantation members at a relatively fixed distance from each other. The central section of the rod member is designed to engage a section of a tissue-engineered matrix implant. In a preferred embodiment, the implantation members have a series of ridges extending out from the outer surfaces of the implantation members to assist in preventing withdrawal from a bone site or other anchoring site after the implantation members are implanted into previously-created bore holes.

Yet another aspect of the present invention is a method of using the graft fixation device of the present invention to affix a matrix containing tissue-engineered tissue to a bone.

Still yet another aspect of the present invention is a graft fixation device combination which is the combination of a fixation device and an insertion member. The fixation device has a first implantation member. The implantation member has a longitudinal axis, a proximal end, a distal end, an outer surface, and a longitudinal passage therethrough. The fixation device also has a second implantation member. The second implantation member has a longitudinal axis, a proximal end, a distal end, an outer surface, and a longitudinal passage therethrough. Each implantation member has a proximal annular face on its proximal end surrounding the longitudinal passages. There is a connecting member connecting the first and second implantation members. The connecting member has a central section, a first end extending from the first implantation member and a second end extending from the second implantation member. There are a pair of insertion devices. Each insertion device is a member having a proximal end, a distal tapered end and a longitudinal passage therethrough. The distal end of each implantation member is in engagement with the proximal end of an insertion device.

Yet another aspect of the present invention is an insertion instrument for inserting the fixation devices and combinations of the present invention in bone. The instrument has a removable distal end housing and removable prongs. The instrument has an elongated member having a proximal end, a distal end, a distal end surface, and an outer surface. Outer screw threads extend out from the outer surface about the distal end. There is a hollow member having a cavity, a proximal end and a distal end, and an outer surface and an inner surface, said hollow member having an opening in the proximal end in communication with the hollow cavity. Inner screw threads extend out from the inner surface of the hollow member. A pair of spaced apart prong holes extend through the distal end of the hollow member, said prong holes being in communication with the cavity. A retention groove extends into the inner surface of the distal end of the hollow member There are a pair of prongs, said prongs having elongated members having distal ends and proximal ends. In a preferred embodiment, a piercing point extending distally from the distal end of each prong. A retention member is mounted to the proximal end of each prong, and the retention member has a proximal surface. The instrument is assembled by inserting the prongs through the prong holes, such that the prongs extend through the prong holes, and the proximal retention members are contained within the retention groove. The hollow member is then screwed onto the distal end of the elongated member, by engaging the mating inner threads with the outer threads, and rotating the hollow member until the distal end surface of the elongated member is in engagement with the proximal surfaces of the retention members.

Still yet another aspect of the present invention is the combination of the insertion instrument as described above and a graft fixation device and combination of the present invention.

A further aspect of the present invention is an instrument for inserting a graft fixation device into bone. The instrument has a mounting member having a first end, an opposed second end, a top and a bottom. There is an elongated slide rod member having a proximal end and a distal end and an outer surface and a longitudinal axis. The distal end of the slide rod is mounted to the first end of the mounting member such that the longitudinal axis of the mounting rod is angulated at an acute angle with respect to the mounting member. A hammer handle member is slidably mounted to the slide rod. The hammer handle has a distal end, a proximal end, an outer surface, a first flange member extending from the proximal end, a second flange member extending from the distal end, an inner passage therethrough and a longitudinal axis. There is a mounting rod having a proximal end and an angulated distal end. The angulated distal end has a longitudinal axis and the proximal end of the mounting rod is mounted to the second end of the mounting member. A pair of spaced apart prongs extends longitudinally from the distal end of the mounting rod. The longitudinal axis of the slide rod is parallel to the longitudinal axis of the angulated distal end of the mounting rod.

Another aspect of the present invention is a method of using the above-described surgical instrument to perform a surgical procedure.

These and other features and advantages of the present invention will become more apparent from the following description and accompanying drawings.

BRIEF DESCRIPTION OF THE DRAWINGS

FIG. 18 is a perspective view of an insertion member useful to insert a graft fixation member of the present invention.

FIG. 19 is an exploded perspective view of an insertion instrument, a graft fixation device, and two insertion members.

DESCRIPTION OF THE PREFERRED EMBODIMENTS

The graft fixation devices of the present invention can be made from conventional bio-compatible materials, including absorbable and non-absorbable materials, as well as biodegradable materials. The non-absorbable materials which can be utilized include conventional biocompatible materials such as stainless steel, polyethylene, Teflon, Nitinol, non-absorbable polymers, other bio-compatible metals, ceramics, combinations thereof and the like. The absorbable materials which can be used to manufacture the graft fixation devices of the present invention will typically include those conventional bioabsorbable or bioresorbable materials known in this art which can be effectively molded or machined. The bio-absorbable and bio-resorbable materials include polylactic acid, polydioxanone, polycaprolactone, polyglycolic acid, polygalactic acid, other known biocompatible bioabsorbable and bioresorbable polymers, ceramics, composites, combinations thereof and the like and equivalents thereof.

Figure 1:
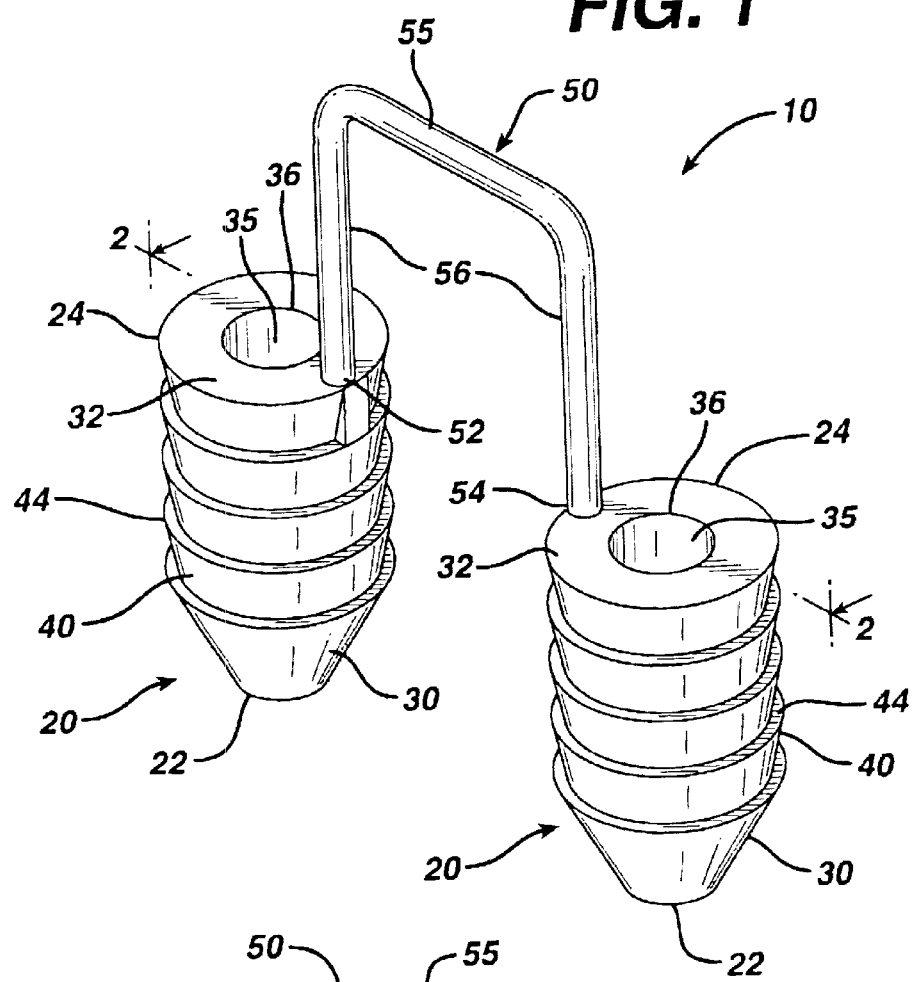
FIG. 1 is a perspective view of a graft fixation device of the present invention.
Figure 2:
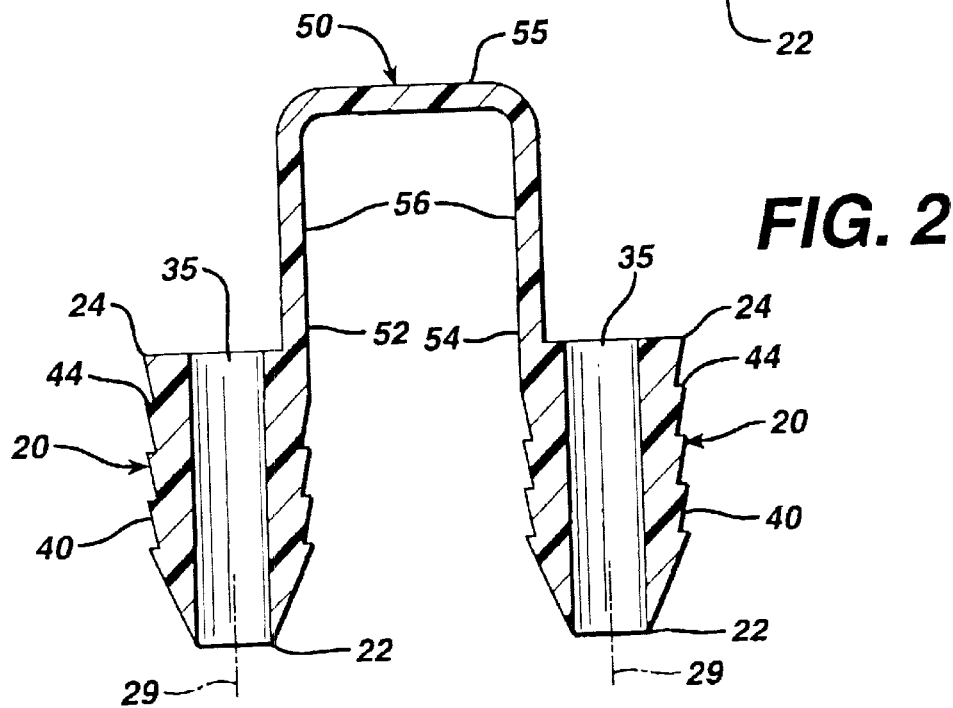
FIG. 2 is a cross-sectional view of the graft fixation device of FIG. 1 taken along view line 2—2.

Referring now to FIGS. 1–2, a preferred embodiment of a graft fixation device 10 of the present invention is illustrated. The graft fixation device 10 is seen to have implantation members 20. The implantation members 20 are seen to be elongated members, preferably having a substantially cylindrical shape. The members 20 may have other geometric shapes including conical, pyramidal, polygonal, cubic, spherical, etc. The implantation members 20 0are seen to have distal ends 22 and proximal ends 24. Each implantation member 20 is seen to have an outer surface 28 and a longitudinal axis 29. Each member 20 is also seen to have longitudinal passage 35 extending therethrough. The implantation members 20 are also seen to have optional frustoconical ends 30, and proximal endface surfaces 32. Although it is preferred that endface surfaces 32 be flat, endface surface 32 may also be angled, concave, convex, etc. Endface surface 32 is seen to have central circular opening 36 in communication with passage 35. Preferably, central opening 36 will have a circular cross-section, but it may have other geometric cross-sections as well including elliptical, polygonal, square, rectangular, combinations thereof and the like. Members 20 are also seen to have distal end face surfaces 37 having circular openings 38 in communication with passages 35. As shown with the optional frustoconical end 30, the annular end face surface 37 is of de minimis thickness around opening 38, however this thickness would increase in the absence of a frustoconical end. Also seen to extend out from the surface 28 of member 20 are a series of optional projections 40 having tissue engagement edges 44. Without the projections 40, the surface 28 of the member 20 will be smooth.

The device 10 is seen to have graft retention member 50 connecting the implantation members 20. Retention member 50 is seen to be a rod-like member having first end 52, second end 54 and central section 55. First end 52 is seen to extend from proximal endface surface 32 of the first member 20 while end 54 is seen to extend up from the proximal endface surface 32 of the other member 20. The ends 54 and 52 of retention member 50 may also if desired extend from or be mounted to any section of outer surface 28. The connecting member 50 is seen to be preferably bent or shaped into three segments including top segment 55 and leg segments 56. The top segment 55 is seen to be substantially perpendicular to the leg segments 56. Although it is preferred that connecting member 50 have an inverted "U" configuration, the connecting member 50 may have other geometric configurations including semicircular, arced, curved, triangular, polygonal, U-shaped, and the like and combinations thereof. The ends 52 and 54 of connecting member 50 may be permanently affixed to the implantation members 20, or may be removably attached thereto in a conventional manner. Member 50 may be rigid or flexible. Member 50 will have a sufficient surface area to effectively retain a tissue-engineered matrix in place on a bone or other body surface. Preferably, connecting member 50 will have a circular cross-section, but may have other geometric cross-sections as well including elliptical, polygonal, square, rectangular, combinations thereof and the like. Member 50 may be rigid or flexible, and may have a single filamentary structure or have multiple interconnected filaments or members.

Figure 3:
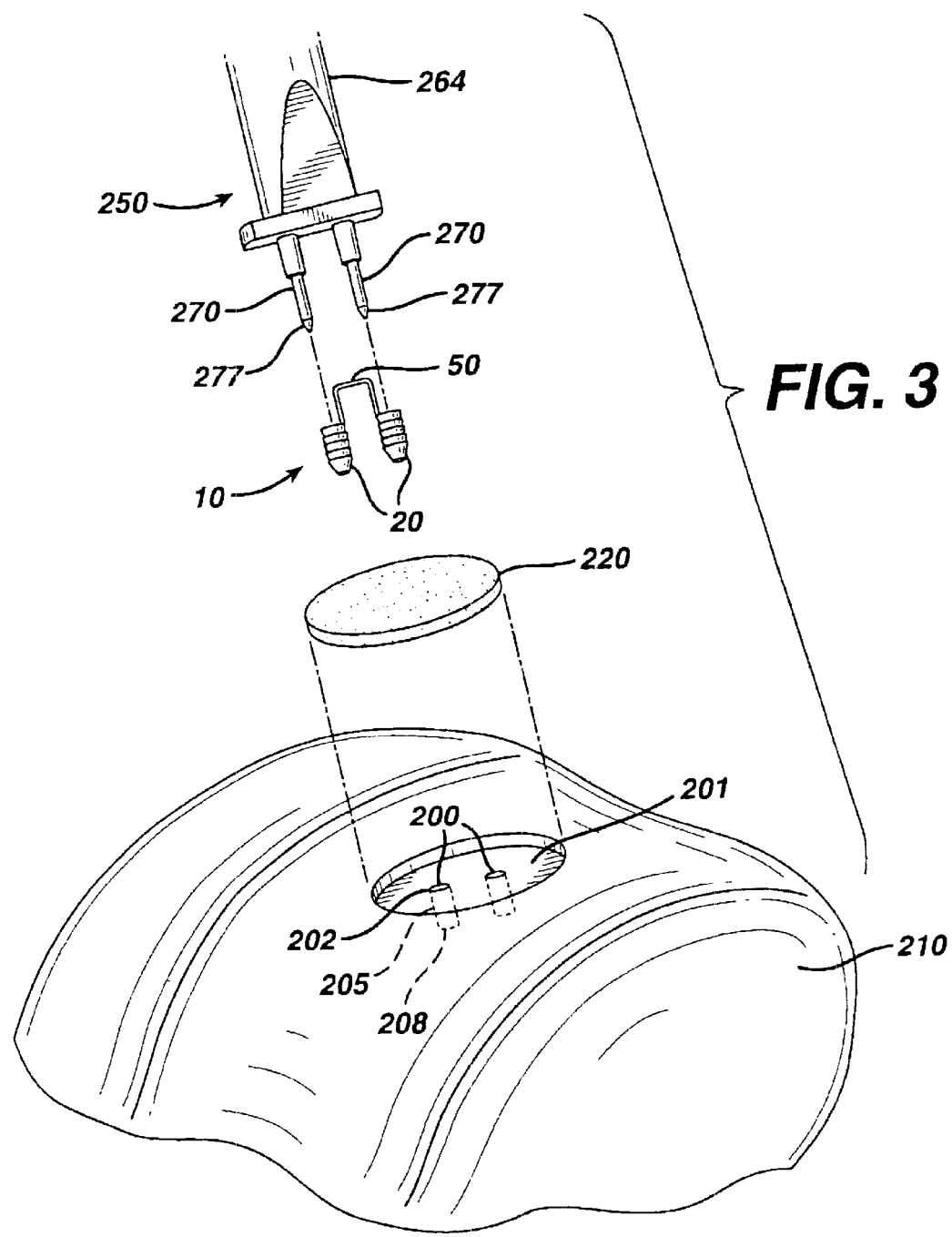
FIGS. 3–6 illustrate a surgical procedure for affixing a matrix to bone using the graft fixation device of the present invention.
Figure 4:
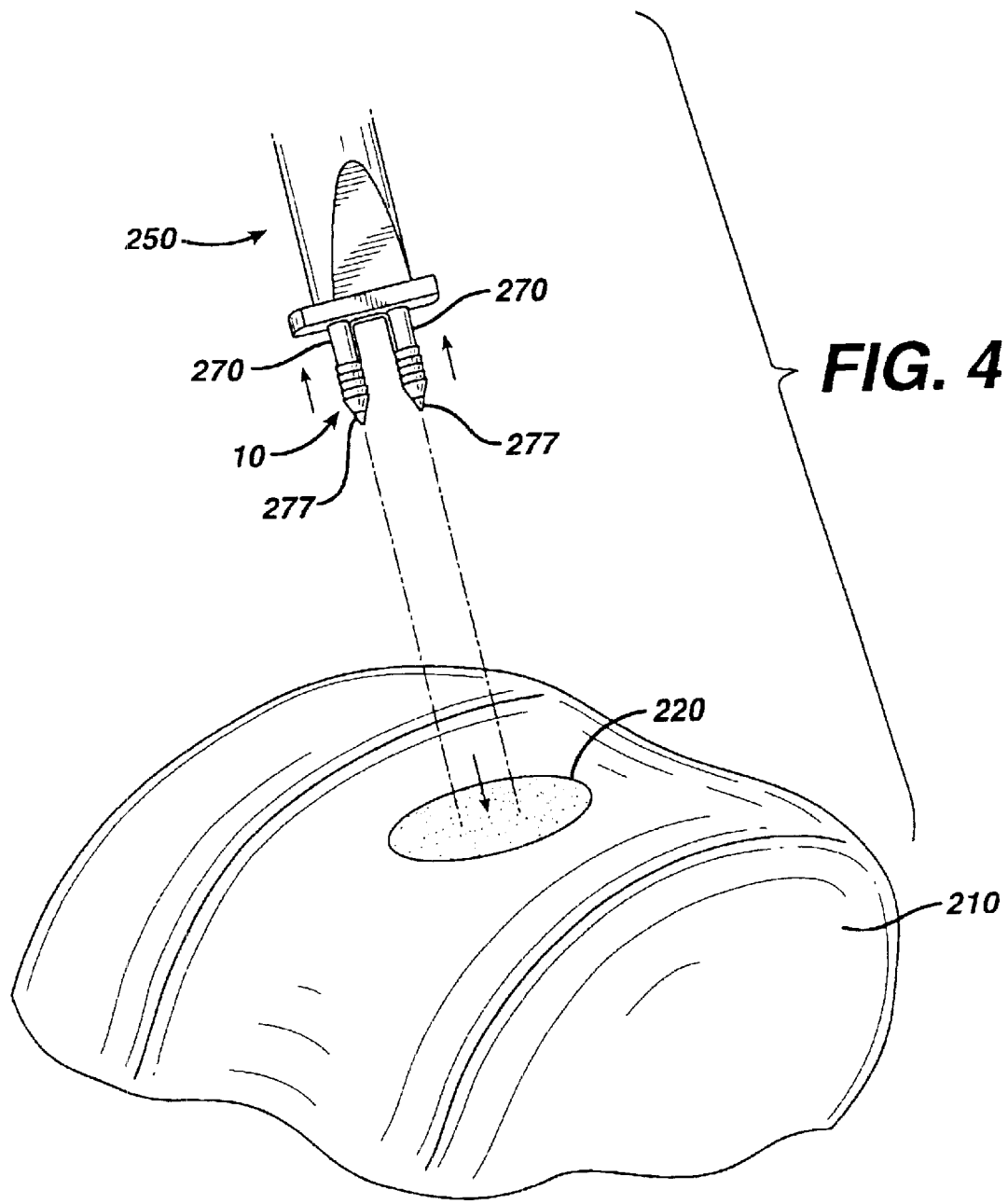
Figure 5:
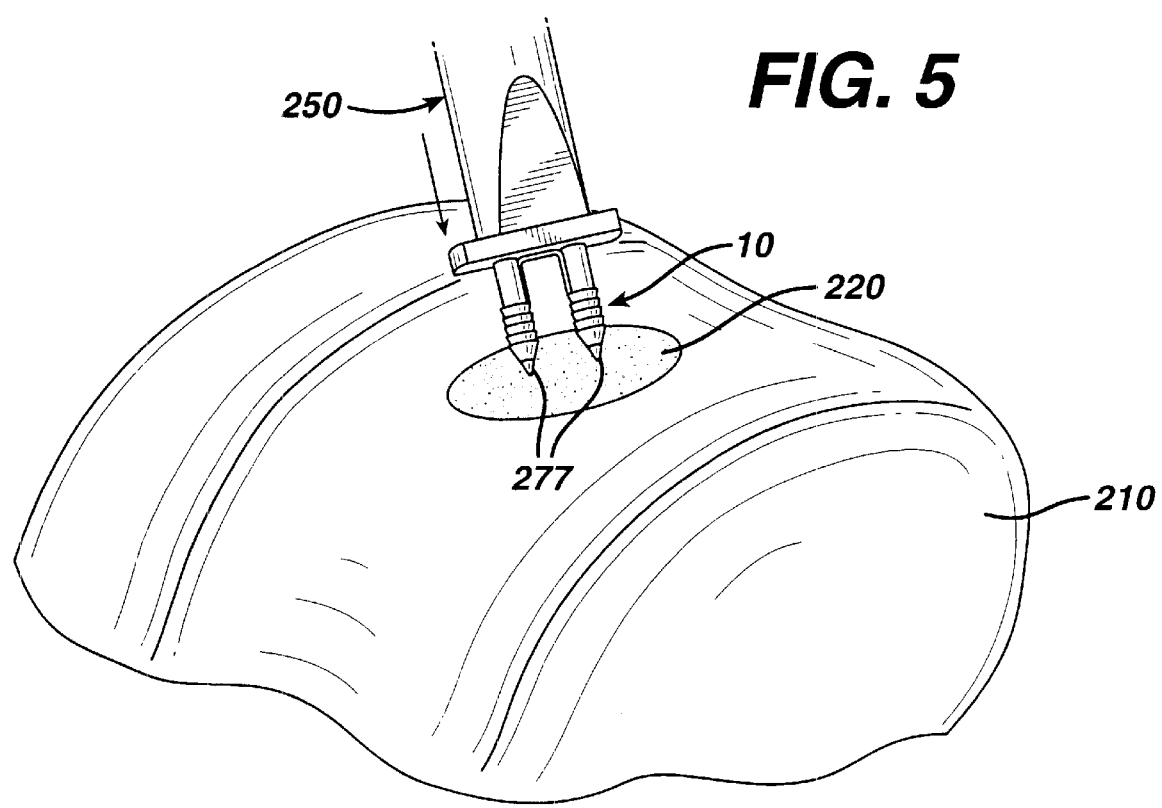
Figure 6:
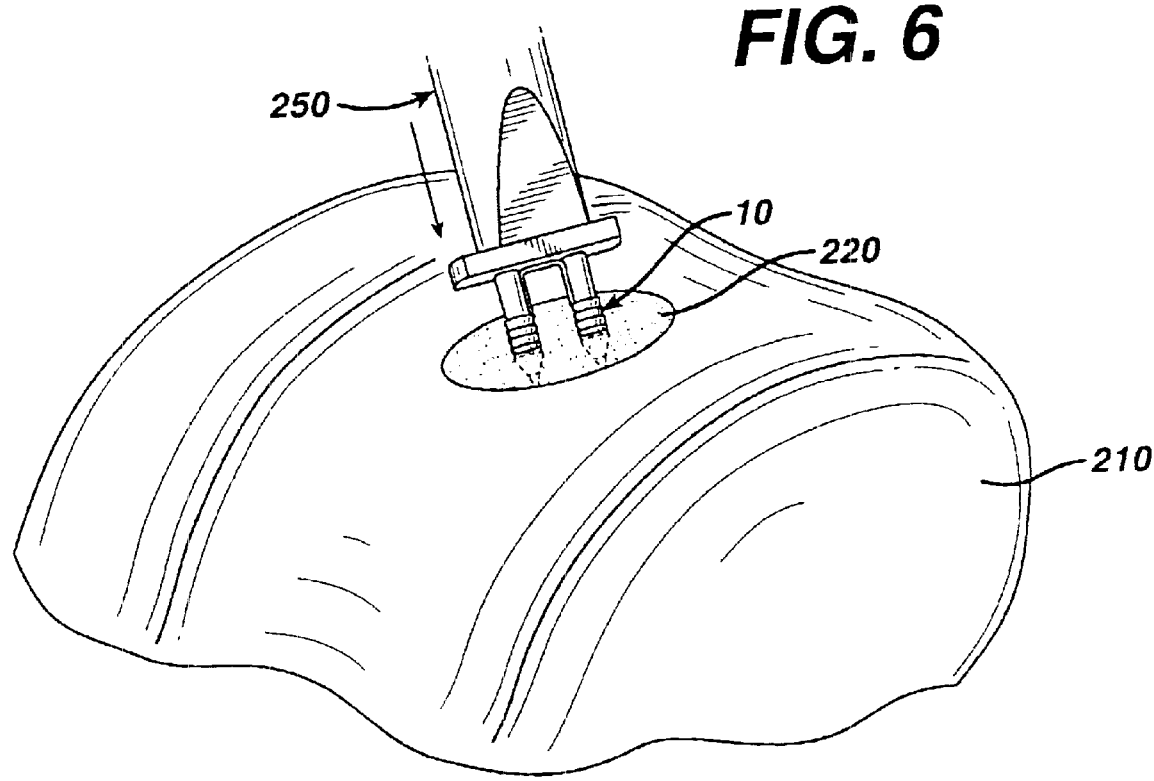
Figure 7:
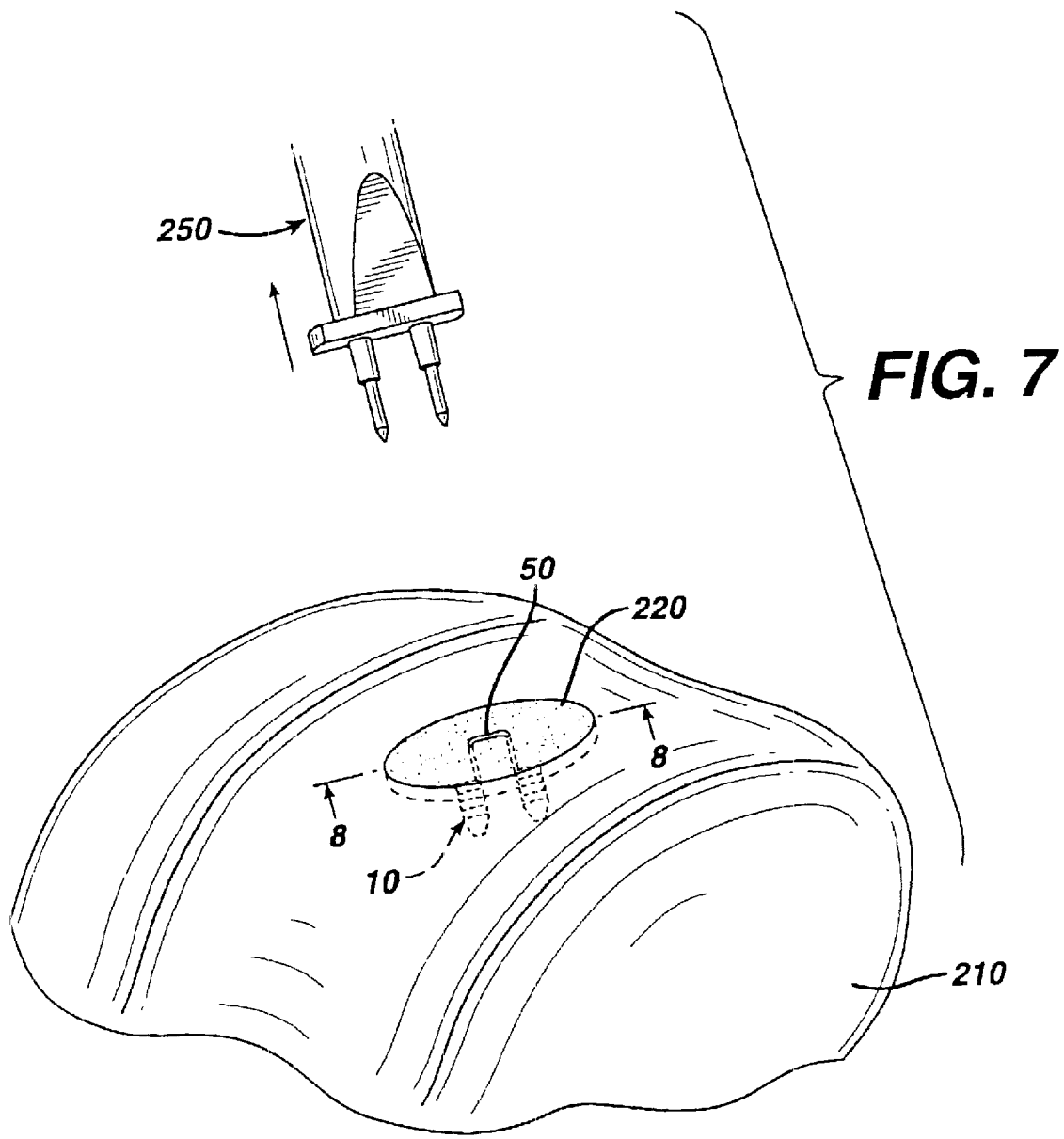
FIG. 7 is an illustration of a graft fixation device of the present invention after the implantation members have been implanted in bore holes in bone illustrating the device affixing a matrix securely to the surface of a bone.
Figure 8:
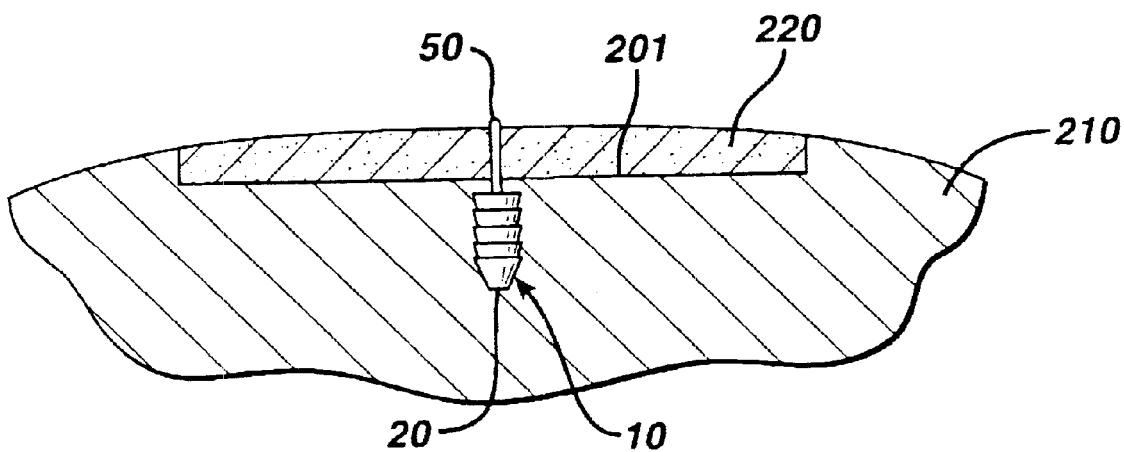
FIG. 8 is a cross-sectional view of the graft fixation device of FIG. 7 implanted in bone, and taken along View Line 8—8.
Figure 10:
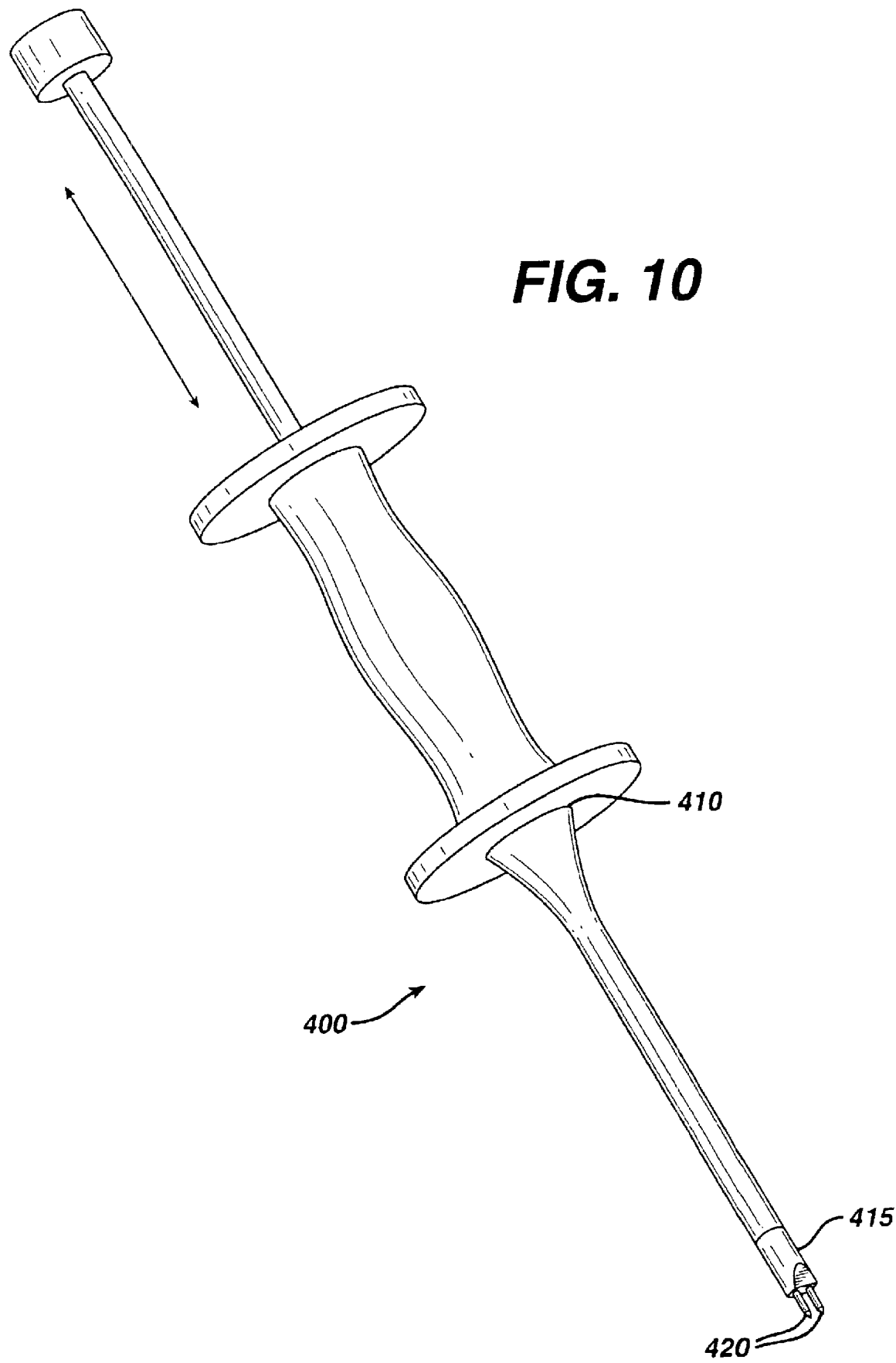
FIG. 10 is a perspective view of an instrument useful for making bore holes in bone into which the implantable members of the graft fixation devices of the present invention may be emplaced.
Figure 11:
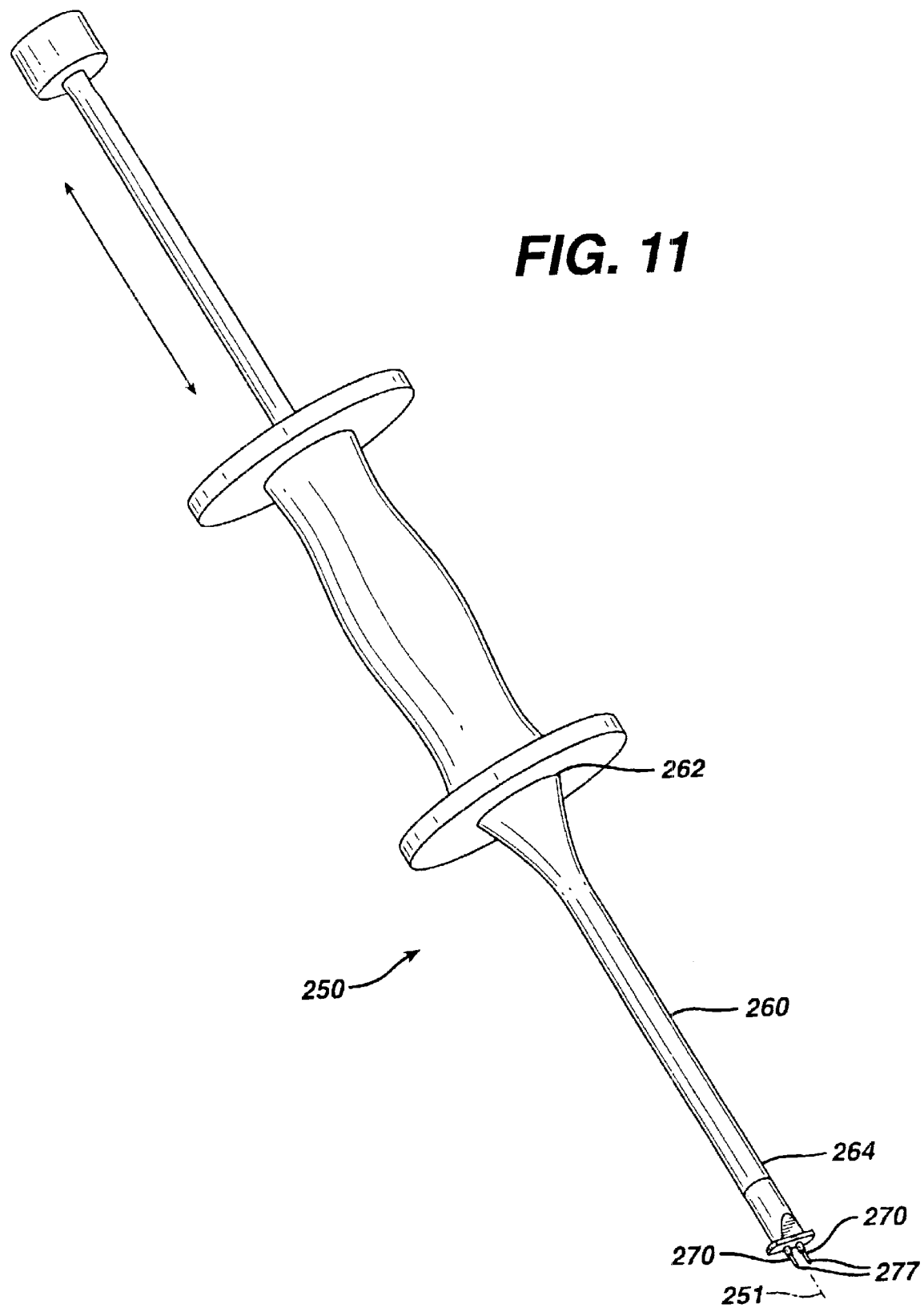
FIG. 11 is a perspective view of an instrument useful for implanting the device of the present invention into bore holes made in bone.

Referring now to FIGS. 3–8, the use of the graft fixation devices 10 of the present invention in a surgical procedure is illustrated. Referring first to FIG. 3, the initial step, prior to the installation of a matrix containing a tissue-engineered tissue using a graft fixation device 10 of the present invention, is to drill or "tap" two bore holes 200 into a bone 210, for example, subchondral bone in the knee joint. The bore holes 200 are seen to be cylindrical holes having a bottom 208 and an open top 202 and side walls 205. Optionally, the bore holes may be bone tunnels with a continuous passage and no bottom, or an open bottom. It is particularly preferred to tap the holes in the bone by using an instrument 400 as illustrated in FIG. 10 which has a proximal section conventionally referred to in this art as a "slap hammer" section. The term "tapping" or "tap" as used herein is defined to mean a procedure wherein the distal pointed prongs 420 extending from the distal end 415 of the shaft 405 of instrument 400 are located over a bone site, and the proximal end 410 of instrument 400 is tapped or hit with slidable hammer handle 450 (of the "slap hammer"), which slides on shaft 460 between proximal end 410 and proximal stop 470, to form the bone bore holes 200. The distal end 465 of shaft 460 is connected to proximal end 411. Proximal stop 470 is mounted to proximal end 467. Hammer handle 450 is seen to have grasping section 451, collars 455 and longitudinal passage 457. Those skilled in the art will appreciate that a similar pointed instrument may be used to "tap" in the bore holes into bone, that is, any instrument having a nail-like distal end. In addition, although not preferred, one bone bore hole at a time may be "tapped" in. If the surgeon decides to drill the bore holes into bone, any conventional surgical drilling apparatus may be used. After the bore holes 200 are formed into the bone 210, the matrix 220 containing tissue-engineering tissue is placed upon the bone surface 201 by the surgeon as seen in FIG. 4. Next, the graft fixation device 10 is mounted on to the insertion instrument 250. Insertion instrument 250, as illustrated in FIG. 11, is seen to be an elongated rod 260 having a proximal end 262 and a distal end 264. Mounted to the distal end 264 of the rod 260 is the depth stop 290. The depth stop 290 is seen to be a substantially rectangular member which is mounted perpendicular to the longitudinal axis 251 of the rod 260. Depth stop 290 is seen to have bottom 292. Extending distally from the bottom 292 of plate member 290 is a pair of parallel, spaced-apart, mounting prongs 270. The mounting prongs 270 are seen to be substantially rod-like members having distal pointed tips 277 and proximal ends 272. The prongs 270 are seen to have first section 273 and distal section 275. Section 273 is seen to have a greater cross-sectional dimension than distal section 275 such that the entire section 275 is insertable into passages 35 of members 20, while proximal section 273 is not insertable therein. Instrument 250 is also seen to have a "slap hammer section" consisting of proximal shaft 300 extending from proximal end 262, slidable hammer handle 320 (the "slap hammer") which is slidable upon shaft 300 between proximal end 262, and proximal stop 330. Hammer handle member 320 is seen to have grasping section 325, end collars 327 and longitudinal passage 329. The graft fixation device 10 is mounted to the insertion instrument 250 by sliding the implantation members 20 onto the prongs 270 such that the distal sections 275 of members 270 are engaged within the longitudinal passages 35 of members 20 and distal points 277 protrude beyond the end of distal endface surfaces 37. Then, as seen in FIGS. 5 and 6, the instrument 250 is manipulated such that the graft fixation device 10 is inserted through matrix 220 and into bone 210 by moving the implantation members 20 mounted on prongs 270 into the bore holes 200 such that the members 20 are engaged in the bore holes 200, and such that the tissue engagement section 55 of the retention member 50 engages the matrix 220 such that the matrix 220 is firmly engaged against the surface 201 of the bone 210. If desired, holes may be cut into matrix 220 prior to insertion of device 10. Then, as seen in FIG. 7, the insertion instrument 250 is withdrawn proximally causing the prongs 270 to be withdrawn from the passages 35 of the implantation members 20, thereby leaving the graft fixation device 10 engaged in the bone bore holes, and causing the matrix 220 to be maintained in engagement with the surface 201 of bone 210. The "slap hammer" section of instrument 250 may assist in removal of the prongs. A cross-sectional view illustrating the device 10 engaged in bone 210 while maintaining the matrix 220 on bone surface 201 is seen in FIG. 8.

Figure 12:
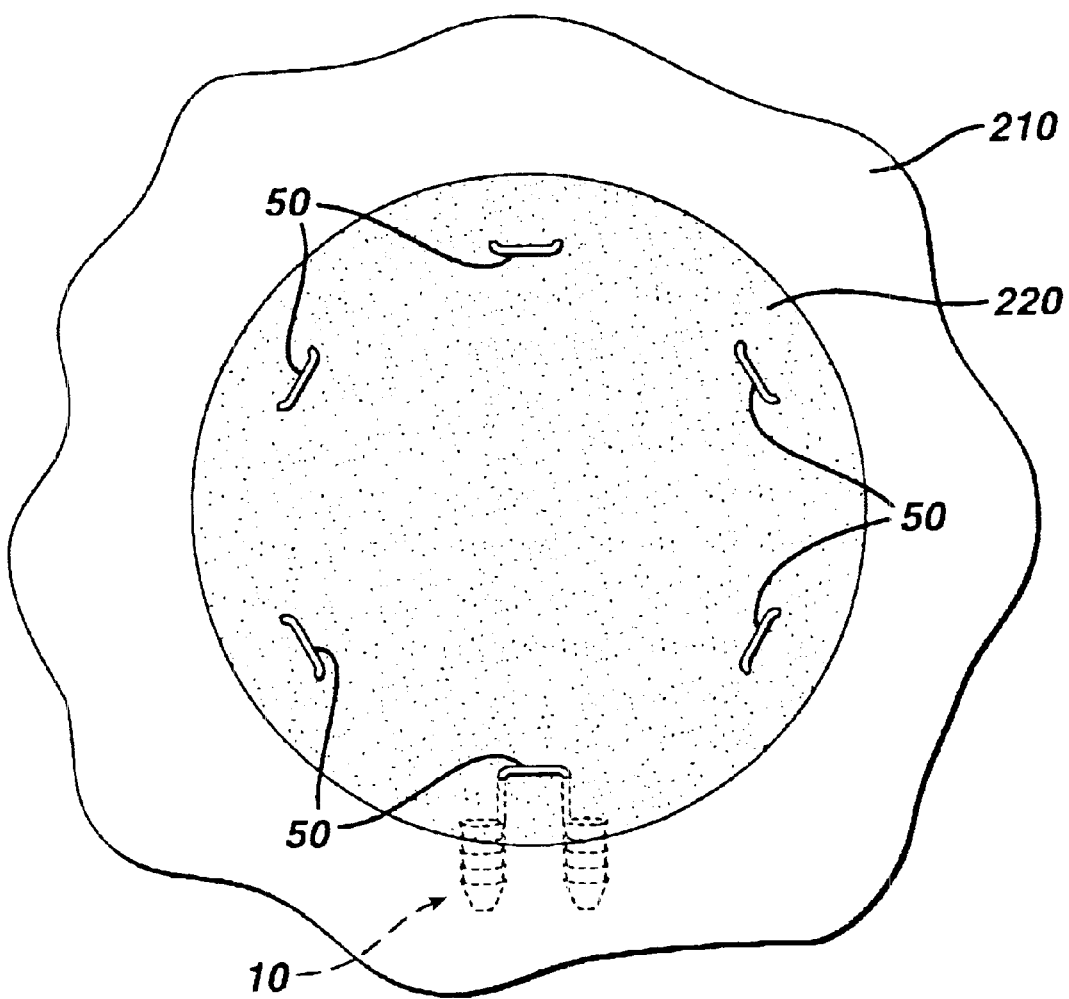
FIG. 12 is a view of a tissue engineered matrix secured to a bone with several graft fixation devices of the present invention.
Figure 13:
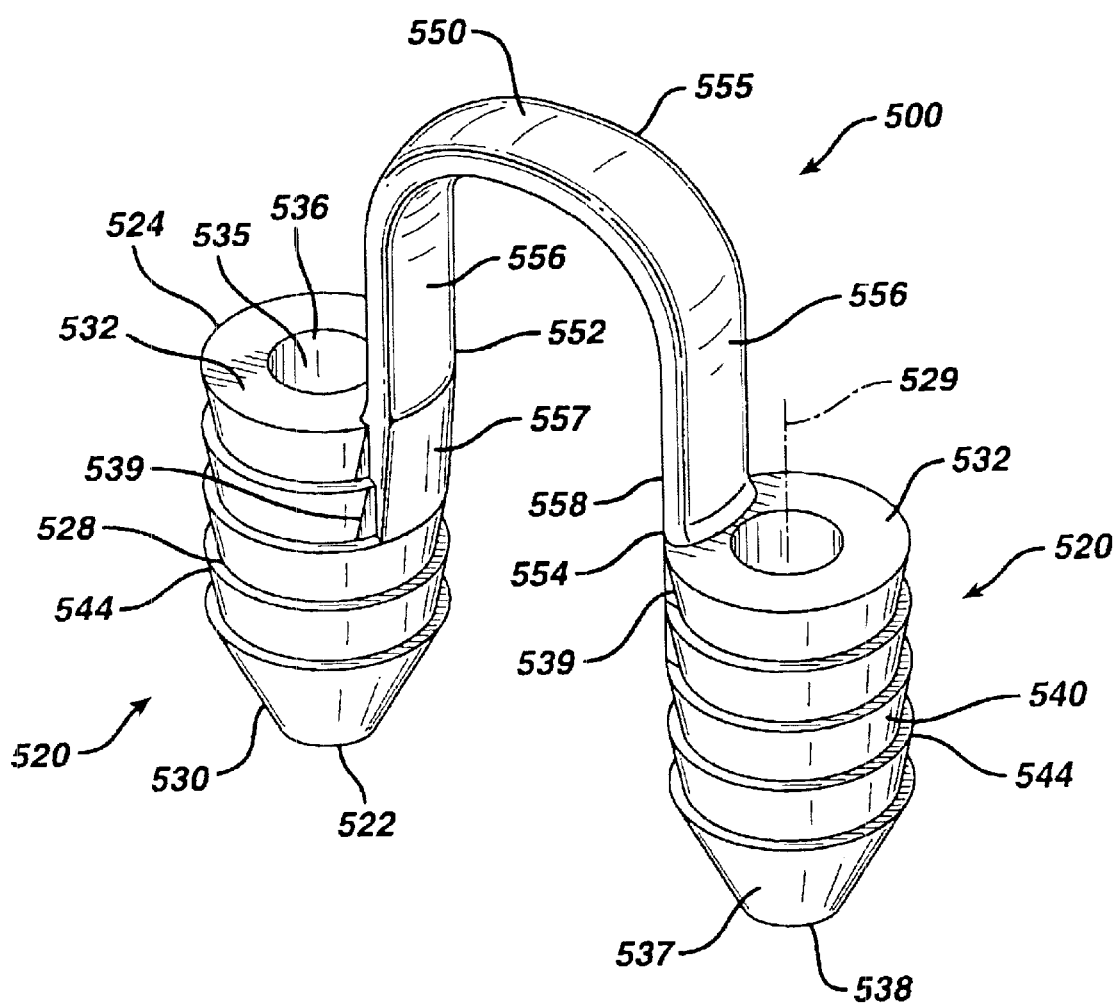
FIG. 13 is a perspective view of an alternate embodiment of a graft fixation device of the present invention.
Figure 14:
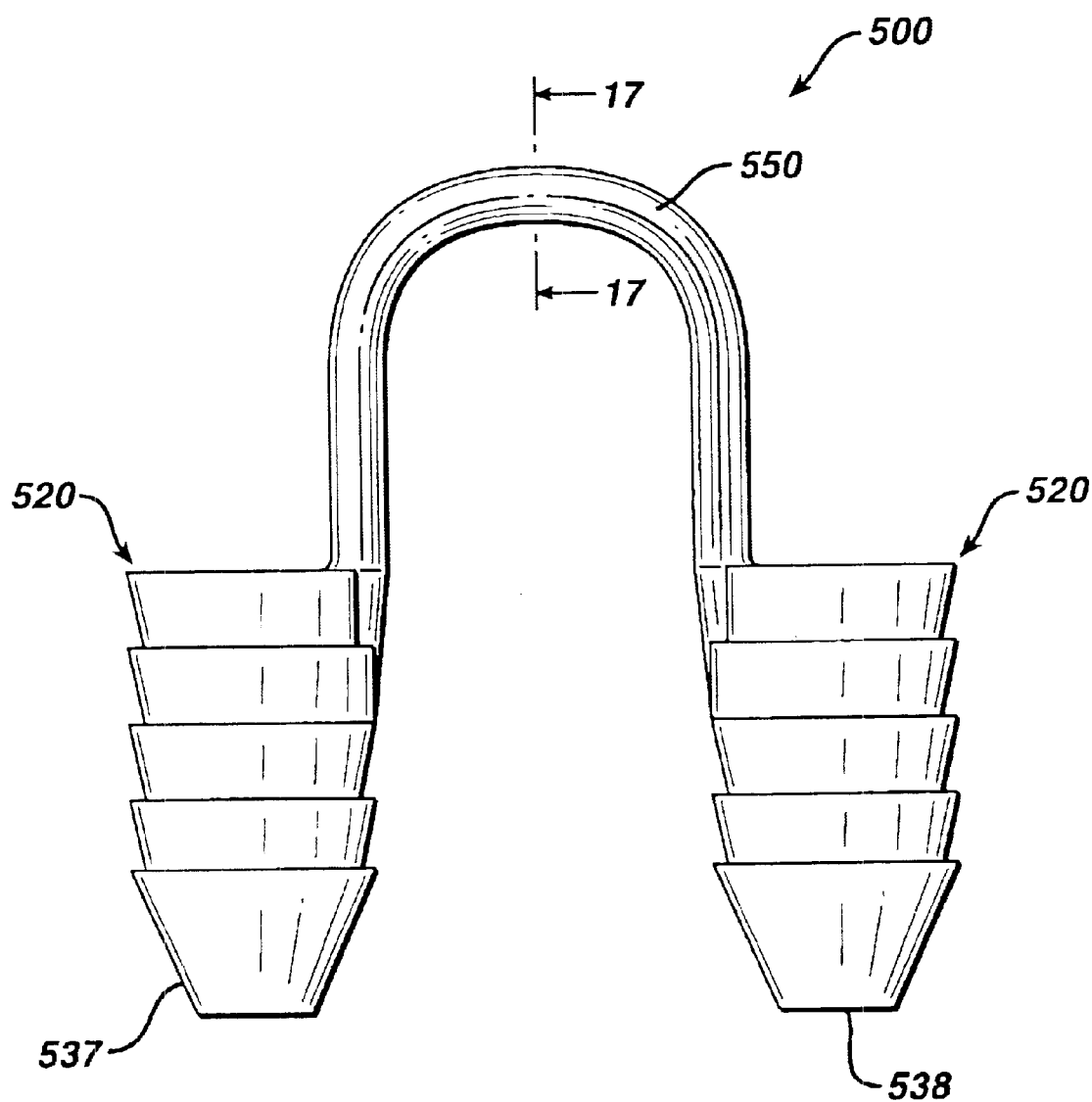
FIG. 14 is a side view of the graft fixation device of FIG. 13.
Figure 15:
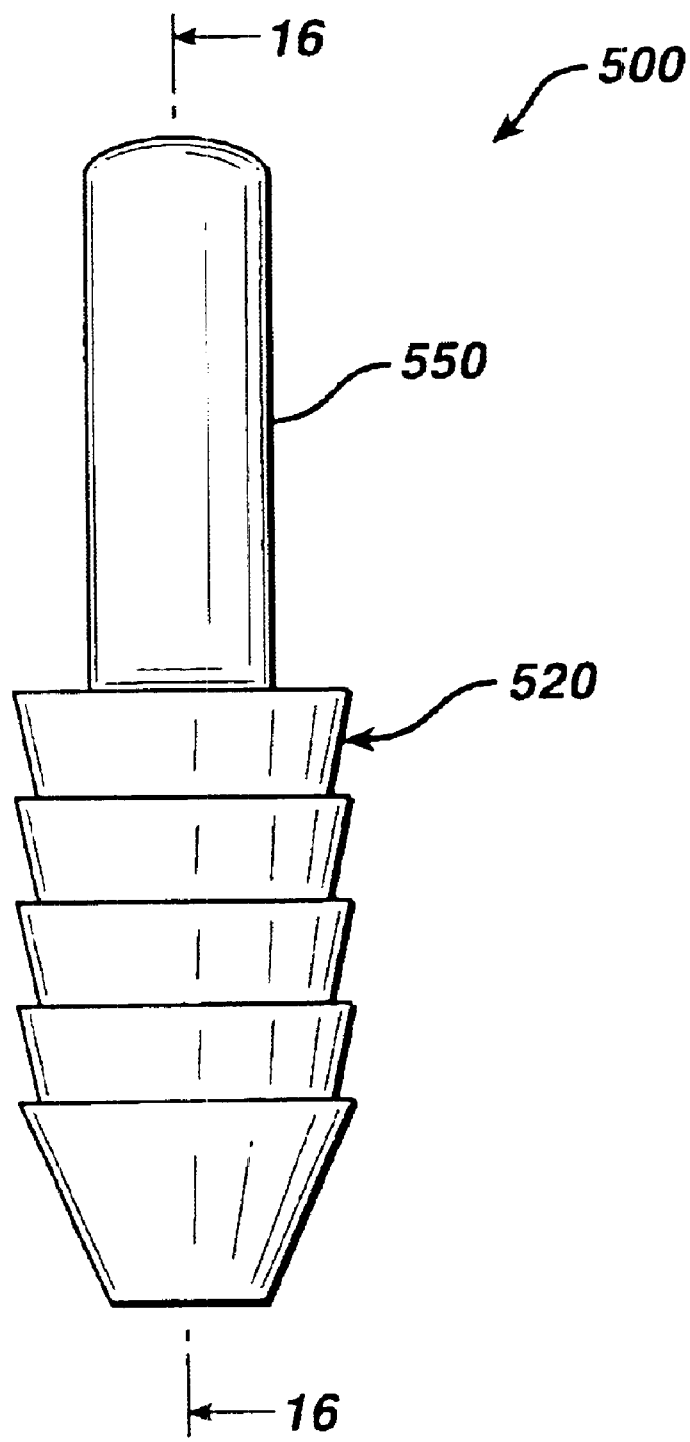
FIG. 15 is an end view of the graft fixation device of FIG. 14.
Figure 16:
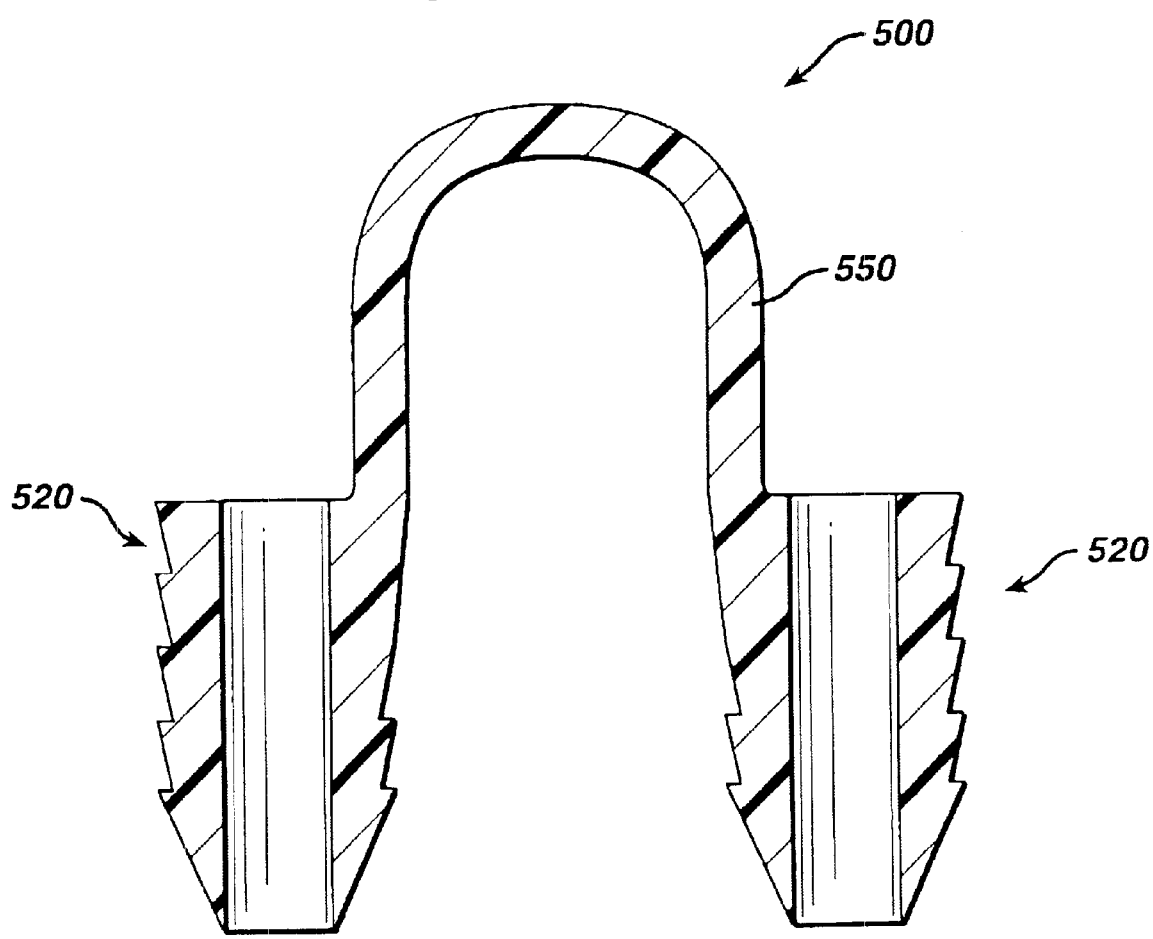
FIG. 16 is a cross-sectional view of the graft fixation device of FIG. 14, taken along View-Line 16—16.
Figure 17:
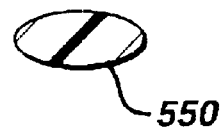
FIG. 17 is a cross-sectional view of the tissue retention member of the graft fixation device of FIG. 14, taken along View-Line 17—17.

FIG. 12 illustrates a matrix 220 mounted to bone surface 201 of bone 210 having multiple fixation devices of the present invention installed to secure the matrix 220. The number, anatomical location and orientation of fixation devices 10 necessary to provide sufficiently effective fixation will vary with the size and type of implant or matrix, the type of tissue, the age of the patient, the size of the patient's defect, the size of the fixation devices, the material of construction of the fixation devices, the load on the tissue at the repair site, etc.

Those skilled in the art will appreciate that the size of the fixation devices of the present invention will vary in accordance with a number of variables including the specific design of the device, the materials of construction, the specific application for the devices, the type of surgical procedure, etc. Similarly, the size of the matrices fixated with these devices will similarly vary. The Figures which are part of this specification are merely schematic and illustrative of the device and method of the present invention; the actual dimensions of the devices and matrices may vary in practice.

The following example is illustrative of the principles and practice of the present invention although not limited thereto.

EXAMPLE

Six sheep were prepared for a surgical procedure using standard aseptic surgical techniques including the use of fully sterilized instruments and equipment, and conventional anesthesia procedures and protocols. The surgeon then created 7 mm diameter chondral (full thickness cartilage) defects on a weight-bearing area of the medial femoral condyle and in the trochlear groove in the right stifle (knee) in each of the six skeletally mature sheep. Defects were created using a specialized drill with a depth-stop to prevent subchondral bone exposure or penetration. The base surfaces of all the defects were then microfractured with a specialized micropick tool to provide access for cellular migration. The subjects were then separated into three groups of two subjects each:

Group 1: defect filled with a collagen matrix, fixed with the graft fixation device of the present invention.

Group 2: defect filled with a collagen matrix, fixed with 9-0 absorbable Vicryl™ suture (interrupted stitch technique, approximately 12 strands per matrix).

Group 3: unfilled defect (control group).

Both defects in a given stifle received the same treatment or served as controls.

For the two sheep in Group 1. after a defect had been created and microfractured, a punch tool 400 was used to create the two requisite bore holes in the subchondral bone to receive one graft fixation device of the present invention. Only one polydioxanone device (4 mm tip-to-tip distance) was used to attach each matrix. To create the bore holes, the punch tool was centered in the defect, oriented in the sagittal plane, and hit or "tapped" with a slap hammer repeatedly until it penetrated several millimeters into the subchondral bone. Next, a 7 mm diameter circular collagen matrix, saturated with saline, was placed in the defect and then blotted dry to remove excess saline. When the inserter tool 250 was loaded with the graft fixation device 10 of the present invention, the device and inserter tool were centered above the matrix and oriented in the sagittal plane. The surgeon then located the previously created bore holes by slowly advancing the distal tips of the inserter through the matrix. Once the surgeon located the holes with the inserter tips, a hammer was used to fully advance the inserter tool (and implantation members 20 of the fixation device 10) through the matrix and into the subchondral bone. The inserter tool had a depth stop to prevent the implantation members 20 from being inserted too deeply, thereby assuring the proper placement of the implantation members through the matrix. The insertion was completed when the connecting retention member between the two implantation members initially started to compress the collagen matrix, thereby indicating secure fixation with the underlying subchondral bone. After the two defects in a given stifle had each been repaired with a matrix and fixation device, the stifle was closed and the sheep was allowed to recover. It was noted by the surgeon that it took approximately one minute to attach a matrix with a fixation device of the present invention (Group 1), versus approximately 15 minutes to attach a matrix with suture alone and the requisite suture manipulation and knot tying (Group 2).

Two weeks after the surgeries were completed, the knee joints were surgically opened for examination. Gross macroscopic assessment of the joints demonstrated that all four matrices held by the graft fixation device of the present invention were fully intact. However, all four matrices held by sutures alone were only partially intact with, on average, approximately 30% of the sutures broken on any given matrix.

Figure 9:
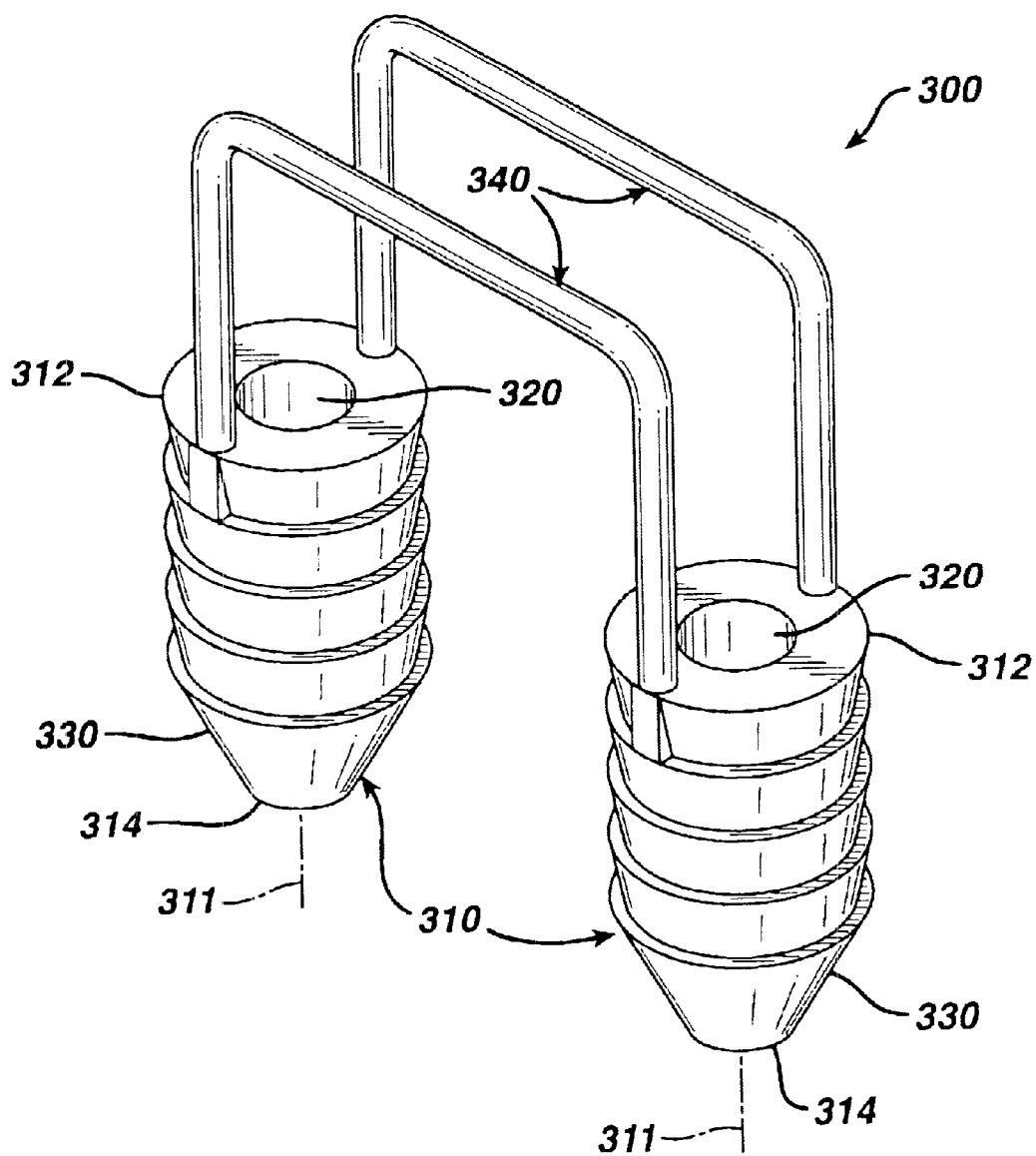
FIG. 9 is an alternative embodiment of a graft fixation device of the present invention having two connecting members.

Another embodiment of the fixation device of the present invention having multiple retention members is seen in FIG. 9. The device 300 is seen to have a pair of implantation members 310. The implantation members 310 are substantially cylindrical members having longitudinal axis 311, distal ends 314 and proximal ends 312. Each implantation member 310 is seen to have a longitudinal passage 320. The members 310 are seen to have a distal frustoconical end 330, outer surface 350, and ridges 355 extending outward from surface 350. The members 310 are seen to be connected by a pair of retention members 340, having first and second ends 342 and 344 respectively.

Yet another embodiment of a fixation device of the present invention is illustrated in FIGS. 13–17. The graft fixation device 500 is seen to have implantation members 520. The implantation members 520 are seen to be elongated members, preferably having a substantially cylindrical shape. The members 520 may have other geometric shapes including conical, pyramidal, polygonal, cubic, spherical, etc. The implantation members 520 are seen to have distal ends 522 and proximal ends 524. Each implantation member 520 is seen to have an outer surface 528 and a longitudinal axis 529. Each member 520 is also seen to have longitudinal passage 535 extending therethrough. The implantation members 520 are also seen to have optional frustoconical ends 530, and proximal end face surfaces 532. Although it is preferred that endface surfaces 532 be flat, endface surfaces 532 may also be angled, concave, convex, etc. Each endface surface 532 is seen to have central circular opening 536 in communication with passage 535. Preferably, central opening 536 will have a circular cross-section, but it may have other geometric cross-sections as well including elliptical, polygonal, square, rectangular, combinations thereof and the like. Members 520 are also seen to have distal end face surfaces 537 having circular openings 538 in communication with passages 535. Preferably, endface surfaces 537 have a sharp edge configuration, but may also have various widths with a rounded or flat configuration. As shown with the optional frustoconical end 530, the annular end face surface 537 is of de minimis thickness around opening 538, however this thickness would typically increase in the absence of a frustoconical end. However, although not preferred, even with a frustoconical, the end surface 537 could have various widths as previously mentioned. Also seen to extend out from the surface 528 of member 520 are a series of optional projections 540 having tissue engagement edges 544. Without the projections 540, the surface 528 of the member 520 will be smooth, however, it will be appreciated that surface 528 could be rough, or could have a variety of conventional projections such as cones, hemispheres, rods, hooks, etc., and the like and equivalents thereof.

The device 500 is seen to have graft retention member 550 connecting the implantation members 520. Retention member 550 is seen to be a band-like member preferably having an oval cross-section. The retention member 550 is seen to have first end 552, second end 554 and central section 555. First end 552 is seen to extend up from proximal endface surface 532 of the first member 520 while end 554 is seen to extend up from the proximal endface surface 532 of the other member 520. A section 557 of end 552 is seen to extend out from section 539 of surface 528, while section 558 of second end 554 is also seen to extend out from a section 539 of surface 528. The ends 554 and 552 of retention member 550 may if desired extend from or be mounted to any section of outer surface 528. The connecting member 550 is seen to be preferably bent or shaped into three segments including top segment 555 and leg segments 556. The top segment 555 is seen to an arc shaped member, and the leg segments 56 are seen to be preferably perpendicular to surfaces 532. Although it is preferred that connecting member 550 have an inverted "U" configuration, the connecting member 50 may have other geometric configurations including semicircular, arced, curved, triangular, polygonal, V-shaped, and the like and combinations thereof. The ends 552 and 554 of connecting member 550 may be permanently affixed to the implantation members 520, or may be removably attached thereto in a variety of conventional manners, for example, a ball and socket joint, a plug joint, etc. Member 550 may be rigid or flexible. Member 550 will have a sufficient surface area to effectively retain a tissue-engineered matrix in place on a bone or other body surface. Preferably, connecting member 550 will have an oval cross-section, but may have other geometric cross-sections as well including circular, elliptical, polygonal, square, rectangular, combinations thereof and the like. Member 550 may be rigid or flexible, and may have a single filamentary structure or have multiple interconnected filaments or members.

Another aspect of the present invention is a distal insertion member (device) useful with the fixation devices of the present invention. As seen in FIG. 18, the insertion device 600 is seen to be a substantially cylindrical member having proximal end 610 and distal end 620, although device 600 may have other configurations as well. Proximal end 610 is seen to have a flat end surface 612. Frustoconical end section 630 is seen to extend distally from distal end 620; although device 600 may have other configurations as well. If desired, distal end 620 can have any tapered or curved configuration, but it is preferred that it have a frustoconical end section extending therefrom. The frustoconical end section 630 is seen to have outer surface 632 and distal tip 640. The member 600 is also seen to have exterior surface 650. Extending through member 600 is the longitudinal passage 660 having first circular opening 665 in communication therewith, and second circular opening 667 in tip 640 in communication therewith. The insertion members 600 are used in combination with the fixation members of the present invention to engage the fixation member in bone simultaneously with tapping the bore holes into bone, thereby eliminating the need for a separate step to form the bore holes prior to inserting the fixation member.

Figure 20:
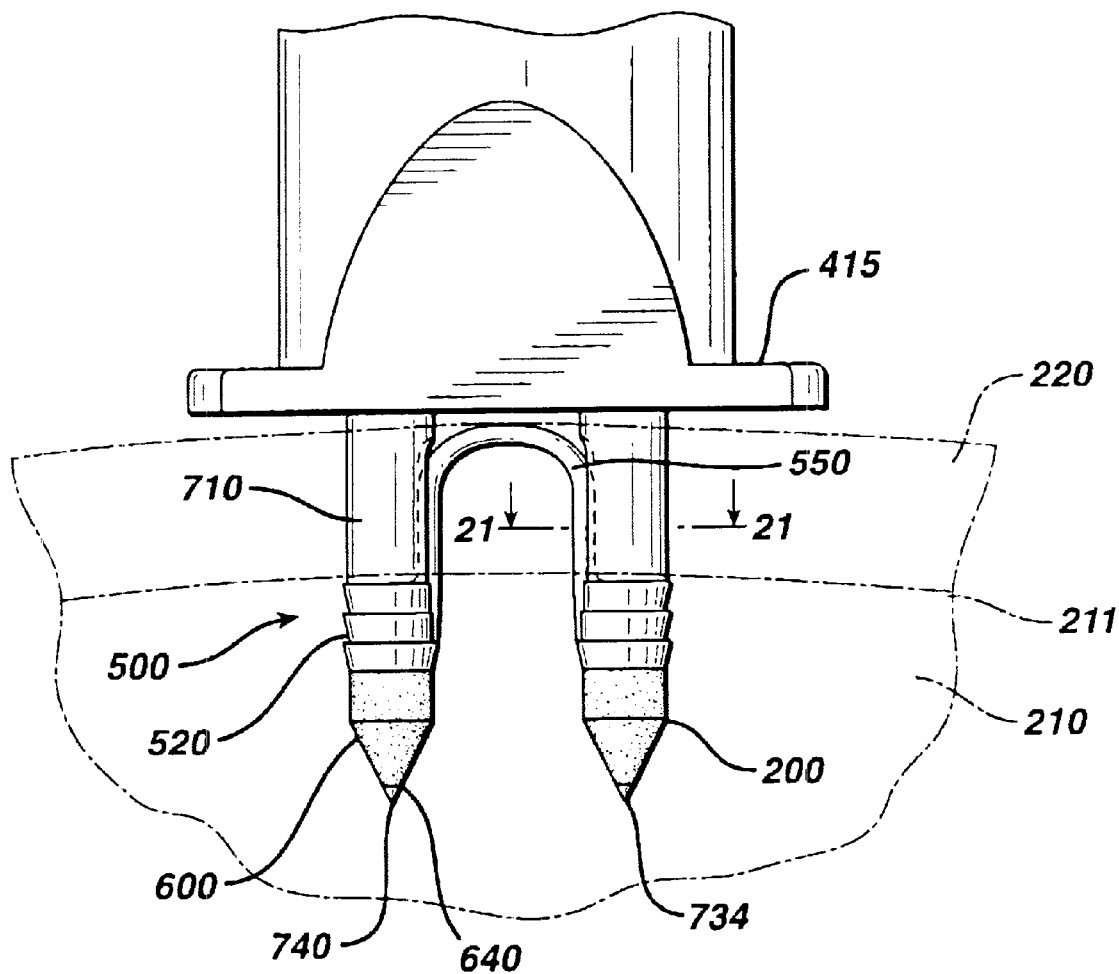
FIG. 20 is a side view of the distal end of the insertion instrument, a graft fixation device, and insertion members engaged in bone, prior to removal of the insertion device.
Figure 21:
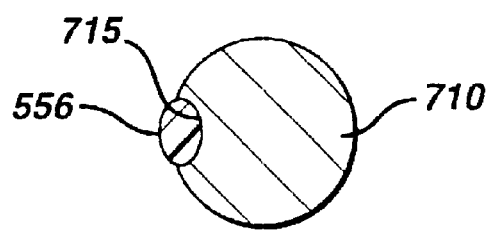
FIG. 21 is a cross-sectional view taken along View-Line 21—21 of FIG. 20 of the prong of the insertion instrument, and a section of the retention member engaged in a longitudinal groove of the prong.

Referring to FIGS. 19–21, the previously mentioned combination of an insertion member 600 and a fixation member 500 is illustrated. Initially, a fixation member 500 is mounted to prongs 700 extending from the distal end 415 of the shaft 405 of instrument 400. Each prong 700 is seen to have first cylindrical section 710 extending from the distal end 415 of the shaft 405. Each cylindrical section 710 is seen to have proximal end 711 and distal end 712, and receiving grooves 715. Extending from the distal end 712 of each first section 710 is the central pin section 720. Central pin section 720 is seen to have proximal end 722 and distal end 724. Extending distally from distal end 724 of central pin section 720 is the distal pin member 730. Distal pin member 730 is seen to have proximal end 732 and distal pointed end 734.

Figure 31:
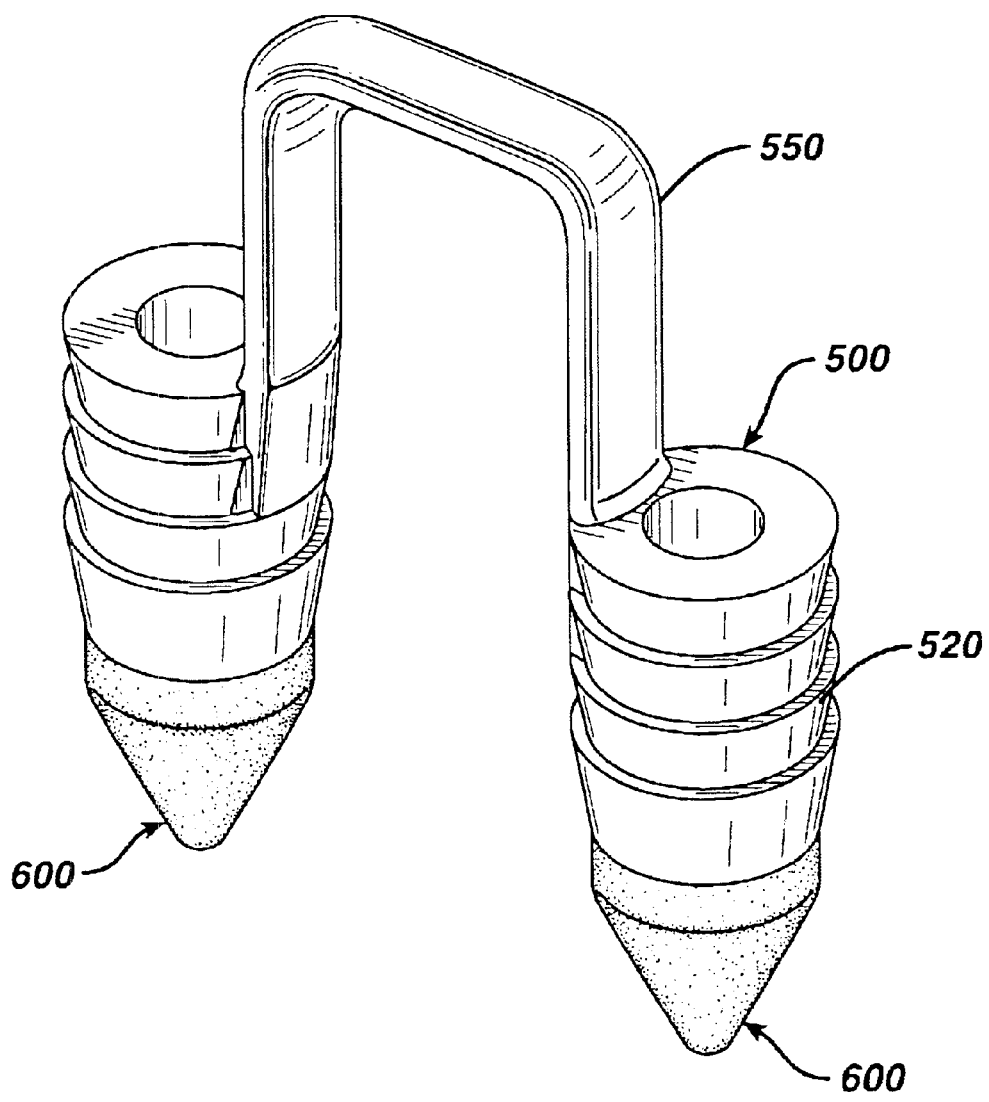
FIG. 31 illustrates a fixation device of the present member having an insertion member molded into the distal end of each implantation member.
Figure 32:
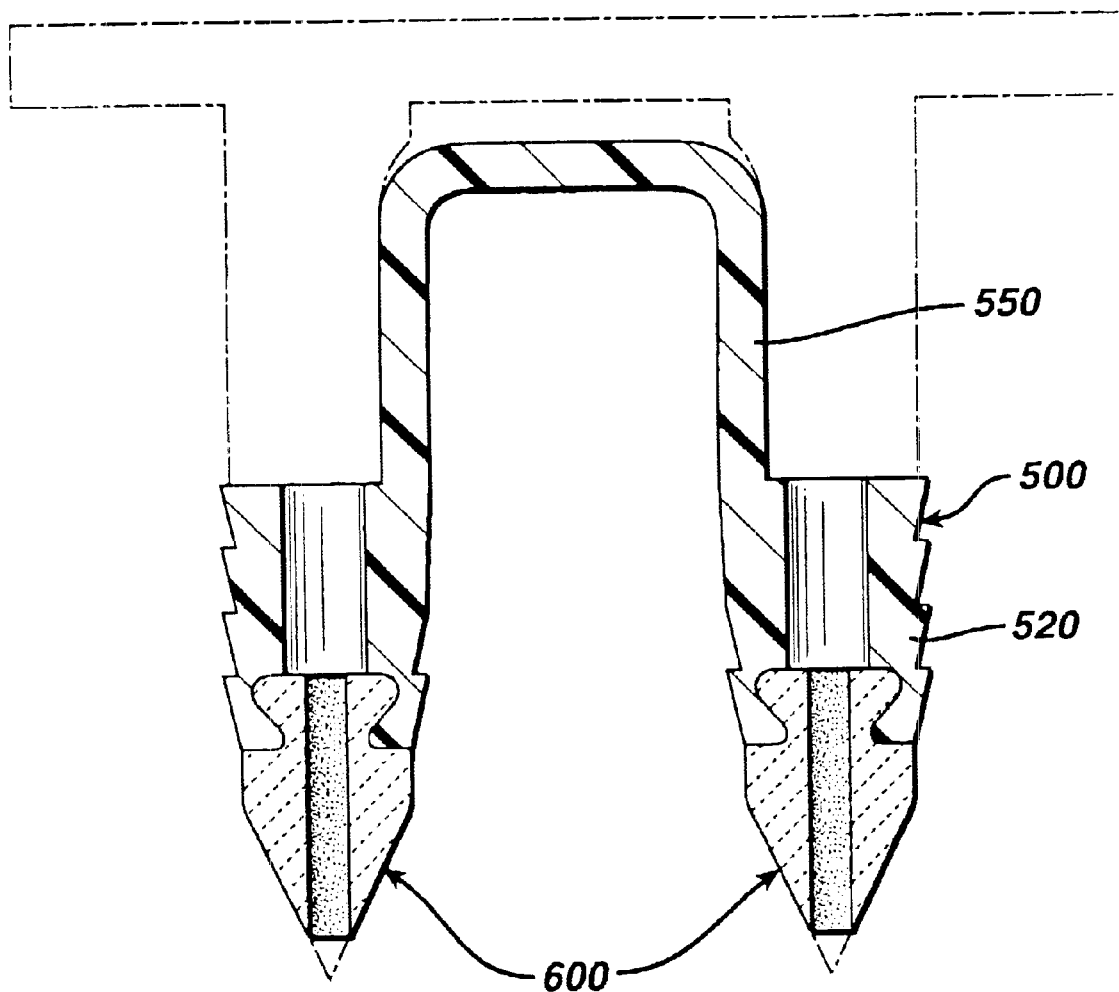
FIG. 32 is a cross-sectional view of the fixation device of FIG. 31.

If desired, the insertion member 600 may be molded into or affixed to the distal end of an implantation member 20, thereby forming a unitary structure as seen in FIG. 31 and FIG. 32. In addition, the insertion member 600 may be mounted to the distal end of an implantation member 520 in a conventional manner by gluing, cementing, mechanical fastening, friction fit, and the like and equivalent thereof.

The combination of the insertion members 600 and fixation members, such as fixation member 500 of the present invention, are used to affix a matrix to bone in the following manner. Initially, the implantation members 520 of a fixation device 500 are placed upon prongs 700 of an instrument 400 such that the leg members 556 are at least partially engaged in grooves 715 in first section 710 (see FIG. 21), and, intermediate sections 720 of pin members 700 are engaged in passages 535 of implantation members 520, while pin members 730 extend out from the distal ends of the implantation members 520. Then, insertion members 600 are placed over the pin members 730, such that the pin members 730 are engaged in passages 660, and such that the pointed piercing ends 734 extend beyond the distal ends 640 of the insertion member 660. Then, the tool 400 and the assembly consisting of fixation device 500 and insertion member 600 is placed over a tissue matrix 220 placed upon a bone 210. The piercing points are then pressed through matrix 220 to contact the surface 211 of bone 210. A slap-hammer section of instrument 400 is engaged to drive the piercing points 734, insertion members 600 and implantation members 520 into the bone 210 as bore holes 200 are formed in the bone. The instrument 400 is then withdrawn proximately, thereby removing the intermediate sections 720 of prongs 700 from the implantation members 520 and the pin members 730 from the insertion members 600, leaving the insertion members 600 and the implantation members 520 securely in the bone (as seen in FIG. 20). This completes the affixation of the matrix 220 to the bone 210 using a single step, wherein the bore holes in the bone are formed simultaneously as insertion members 600 and fixation device 500 are emplaced in the bone.

It is particularly preferred to use conventional remote visualization surgical procedures when inserting the fixation devices of the present invention. For example, inserting a scope through a trocar cannula into the joint or body cavity, while insufflating the body cavity or joint.

The insertion members 600 will typically be made from a strong, hard, bioabsorbable material such that they can be driven into bone without fracturing or breaking. Examples of the types of materials which can be used to make the insertion member 600 include polylactic acid, tricalcium phosphate, calcium phosphate, tetracalcium phosphate and hydroxyapatite, and any copolymers, mixtures or blends thereof. Although not preferred, it is possible to make the insertion members from a conventional biocompatible material which is not bioabsorbable or biodegradable, such as titanium, stainless steel, ceramics, Nitinol and the like and equivalents thereof. The insertion member 600 assists in forming the bore holes 200 while protecting the implantation members 520.

Figure 22:
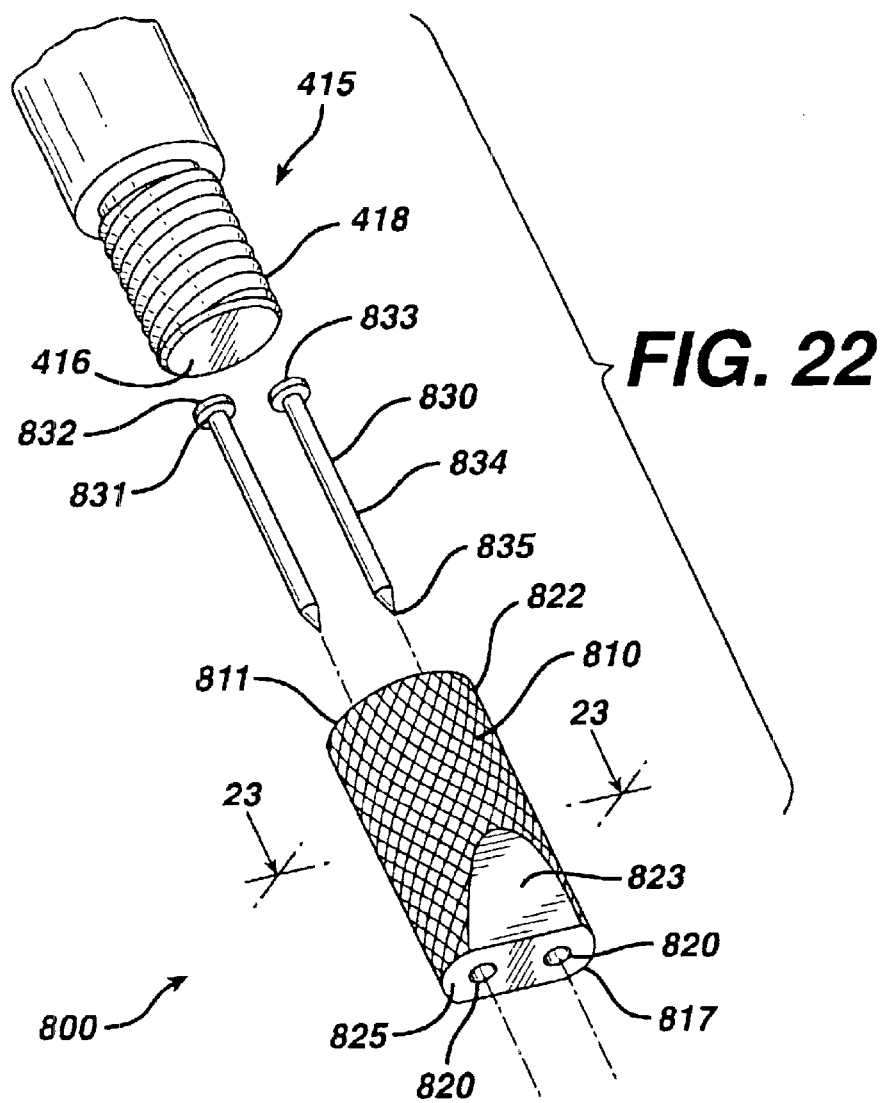
FIG. 22 is an exploded perspective view of the distal end of an insertion instrument of the present invention, illustrating a removable distal end assembly for creating bore holes in bone for receiving the fixation devices of the present invention, wherein the assembly has an end member and pins.
Figure 23:
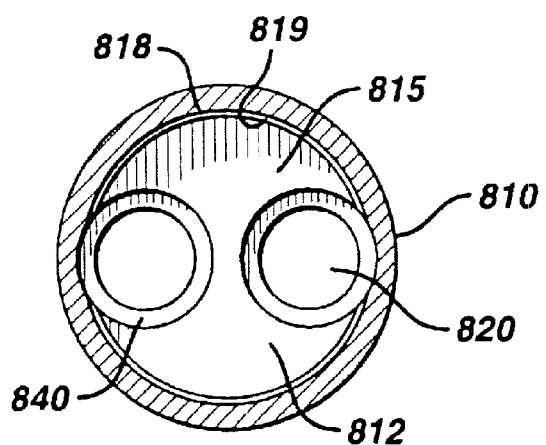
FIG. 23 is a cross-section of the assembly end member of FIG. 22, taken along View-Line 23.
Figure 24:
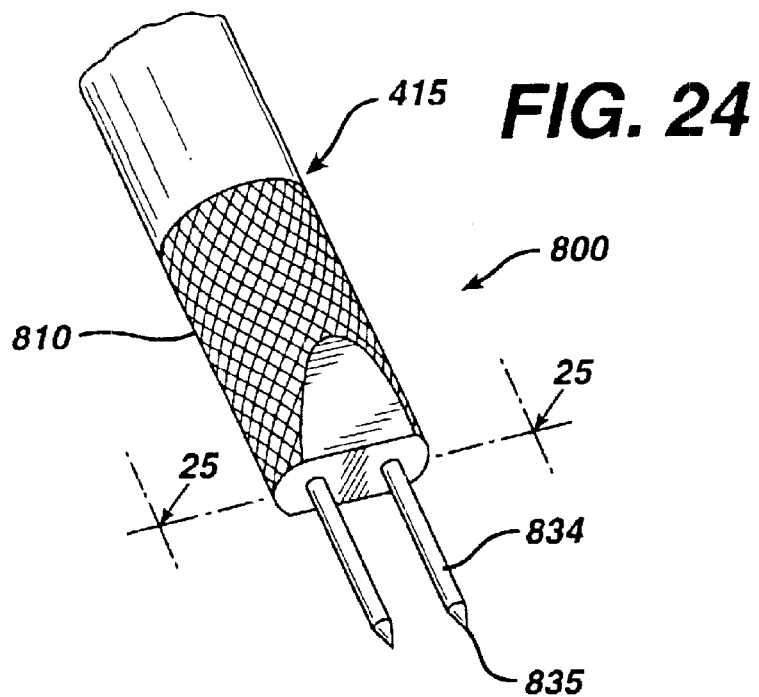
FIG. 24 is a perspective view of the assembly end of FIG. 22, completely assembled and ready for use.
Figure 25:
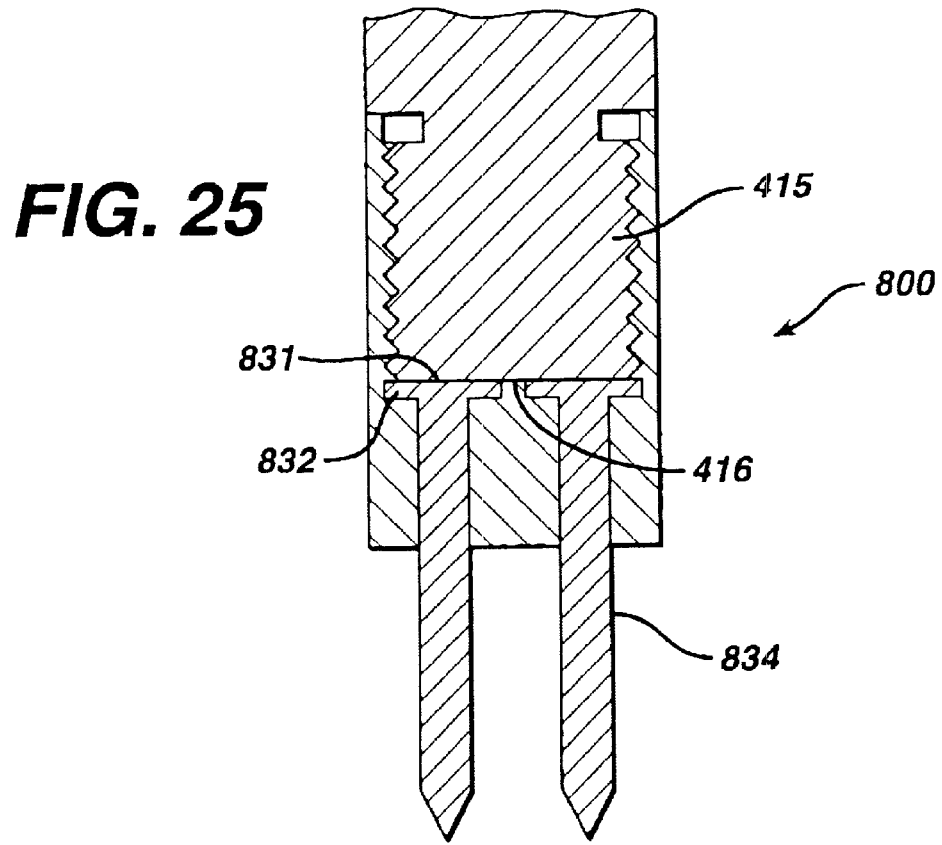
FIG. 25 is a cross-sectional view of the end assembly of FIG. 24, taken along View-Line 25—25.
Figure 26:
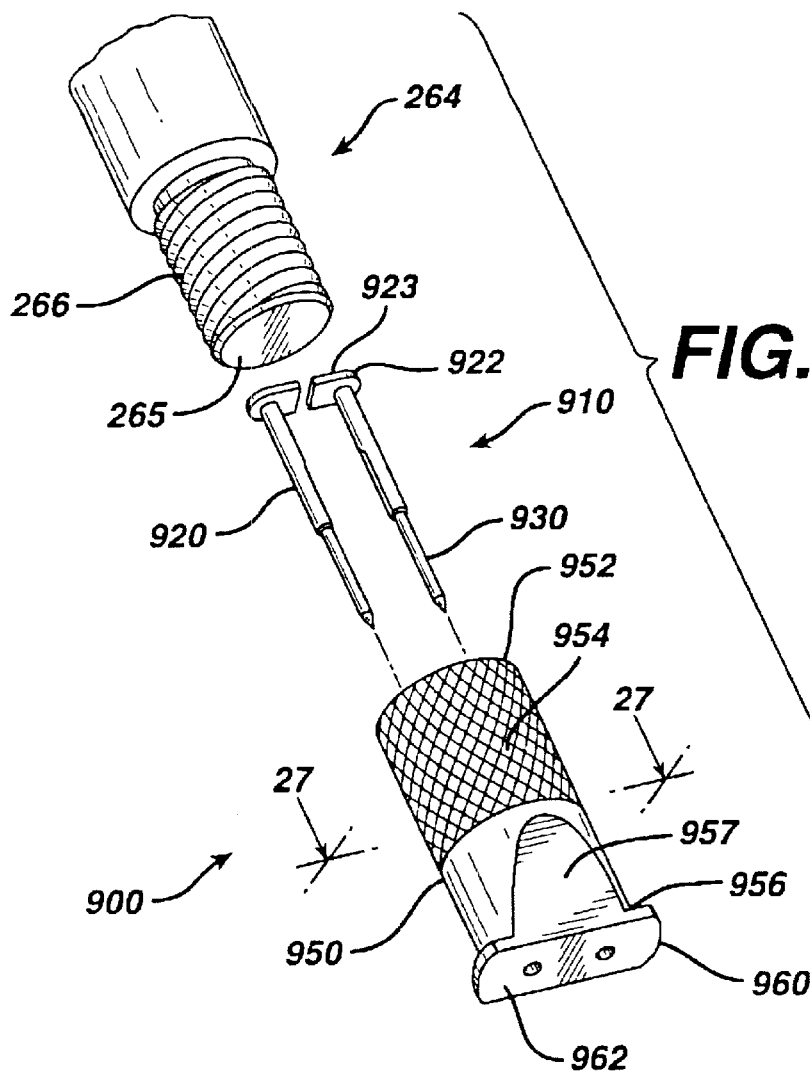
FIG. 26 is an exploded perspective view of an insertion instrument of the present invention having a removable distal end assembly useful for inserting the graft retention members of the present invention into bore holes in a bone, having an end assembly member and two pins; when used with insertion members, the instrument can be used to emplace the fixation devices directly into bone without first forming bone bore holes.
Figure 27:
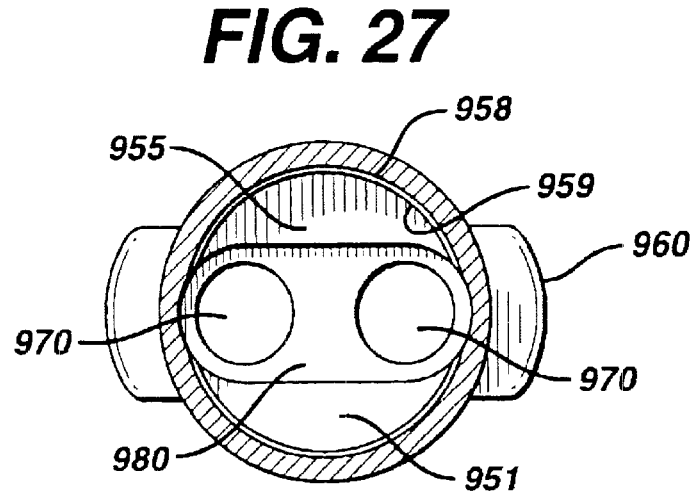
FIG. 27 is a cross-sectional view of the end assembly member of FIG. 26.
Figure 28:
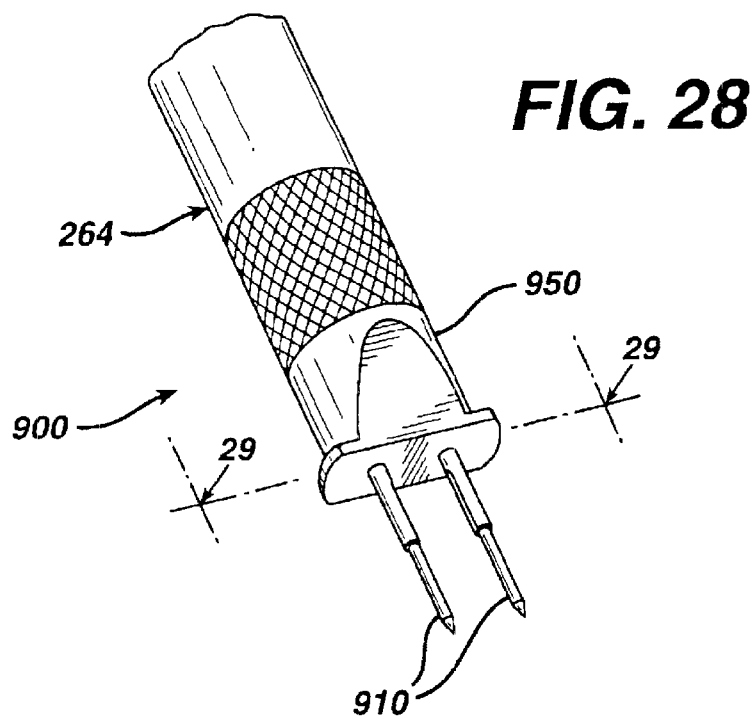
FIG. 28 is a perspective view of the distal end of the insertion instrument of FIG. 26, having the end assembly member and prongs fully assembled and mounted.
Figure 29:
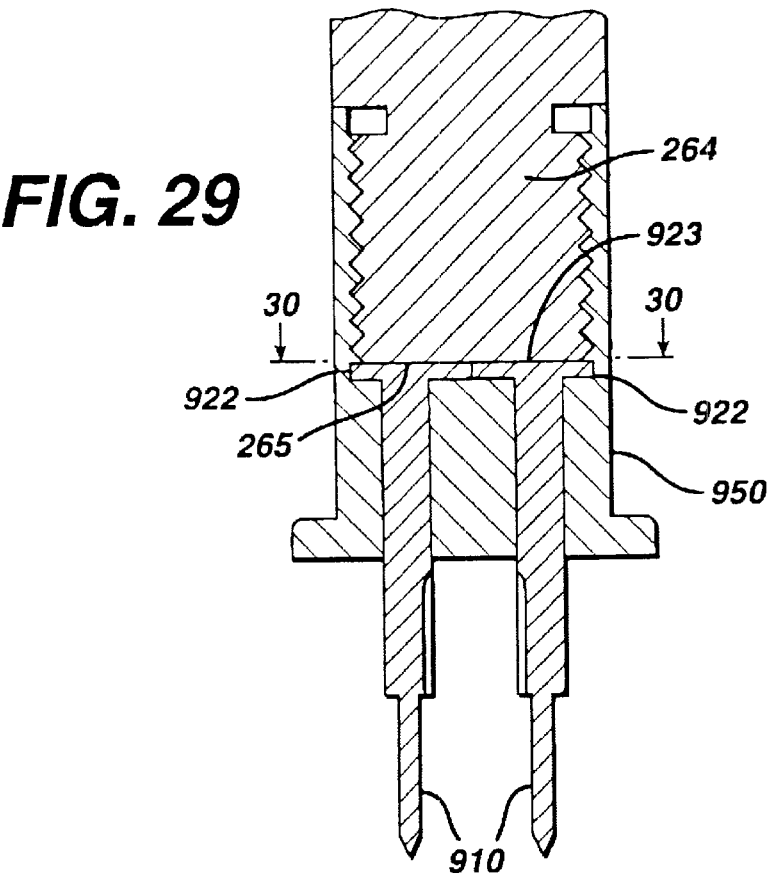
FIG. 29 is a cross-sectional view of the distal end of the insertion instrument of FIG. 28 take along View-Line 29—29.
Figure 30:
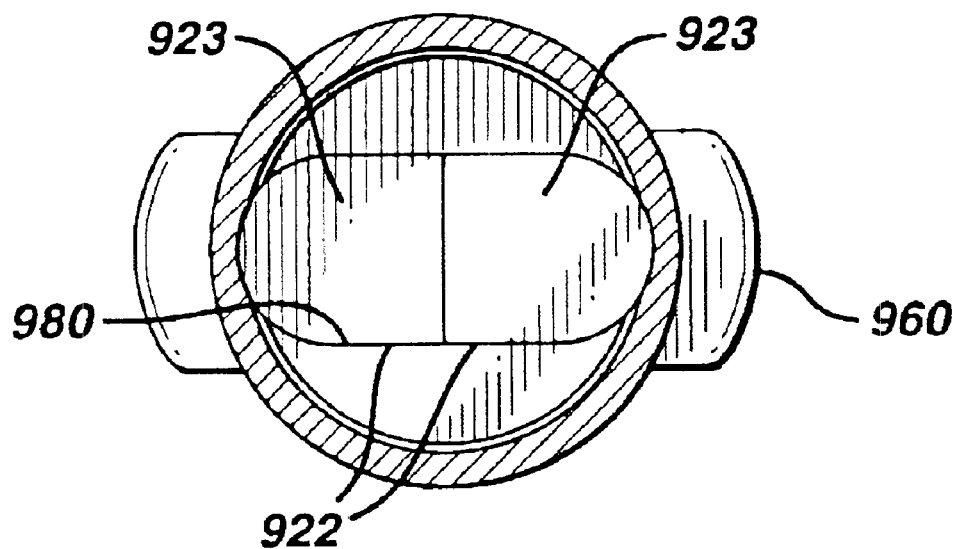
FIG. 30 is a cross-sectional view of the instrument of FIG. 29 taken along View-Line 30—30.

FIGS. 22–23 illustrate a disposable distal end assembly 800 for an instrument 400 of the present invention. When using the disposable assembly 800, it is preferable that the distal end 415 of the shaft 405 of instrument 400 have screw threads 418, although other conventional detachable mounts may be used, for example a bayonet-type mount, locking levers and tabs, male and female mating sections, etc. As seen in FIGS. 22–25, the assembly 800 consists of housing 810 having proximal end 811 and distal end 817. Housing 810 is seen to have hollow cavity 815 therein. Cavity 815 is seen to be in communication with proximal end opening 812 and distal end openings 820. Member 810 is seen to have outer surface 822. Outer surface 822 is preferably knurled to facilitate the grasping and turning of the housing 810. Housing 810 is further seen to have distal end surface 825. The outer surface 822 is seen to have a tapered section 823 which tapers toward end face 825. Contained within cavity 815, on inner surface 818 are the screw threads 819. Assembly 800 is also seen to have driving pin members 830. Each driving pin member 830 is seen to have proximal disk member 832 mounted to proximal end 831, shaft section 834 and distal pointed end 838. Surrounding each opening 820 on the interior of the member 810 are the annular recesses 840. The assembly 800 is mounted to the distal end 415 of the instrument 400 in the following manner. The pins 830 are inserted into cavity 815 and through openings 820 such that the shafts 834 and distal piercing points 838 extend through end face 825, and the disk members 832 are contained within the annular recesses 840. Then, the housing 810 is mounted upon the threads of distal end 415 such that threads 418 engage mating threads 819, and screwed further such that the proximal end surfaces 833 of the disk members 832 are in contact with the distal end face 416 of distal end 415. After use in a surgical procedure, the assembly 800 is removed and discarded. A new sterile assembly 800 is utilized with a cleaned and sterilized instrument 400 for each new procedure.

Referring now to FIGS. 26–30, a disposable end assembly 900 for mounting to an insertion instrument 250 is illustrated. The insertion member 250 is seen to have distal end 264, having endface 265 and screw threads 266. The assembly 900 is seen to have housing 950. Housing 950 has proximal end 952 and distal end 956 and exterior surface 954. The exterior surface 954 is seen to have optional knurling, and distal tapered section 957 tapering into plate member 960. Extending from distal end 956 is the plate member 960. Plate member 960 is seen to have distal surface 962. Housing 950 is seen to have internal cavity 955. Housing 950 is also seen to have proximal opening 951 in communication with cavity 955 and distal openings 970 also in communication therewith. Housing 950 is seen to have internal screw threads 959 extending from internal surface 958. Also contained within the interior of housing 950 in the distal end 956 is the recessed groove 980. Assembly 900 is mounted to the distal end 264 of instrument 250 in the following manner. Pins 910 are inserted through cavity 950 and openings 970 such that proximal members 922 are engaged in groove 980. Sections 920 and 930 of pins 910 extend through openings 970. Sections 920 are seen to have grooves 925. Then, the housing 950 is screwed on to distal end 264 such that the threads 266 engage the mating internal threads 959 of housing 950. The housing is tightened until the distal end surface 265 of the distal end 264 engages the top surfaces 923 of members 922. After a surgical procedure, the assembly 900 is removed from instrument 250 and discarded. A new sterile assembly 900 is utilized with a cleaned and sterilized instrument 250 for each new procedure.

Figure 33:
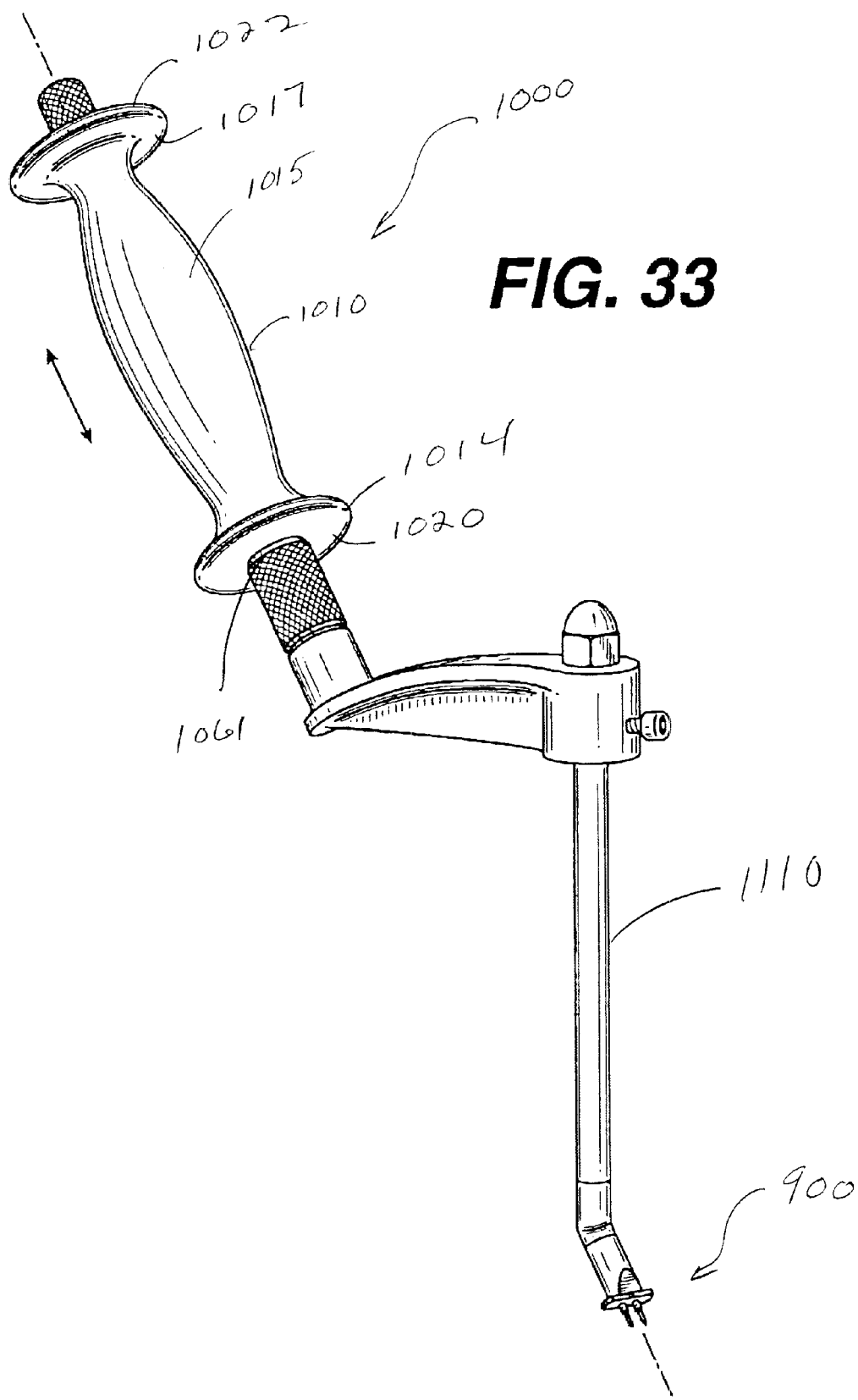
FIG. 33 is a perspective view of a novel combination slap-hammer and insertion instrument useful to insert the fixation devices of the present invention.
Figure 34:
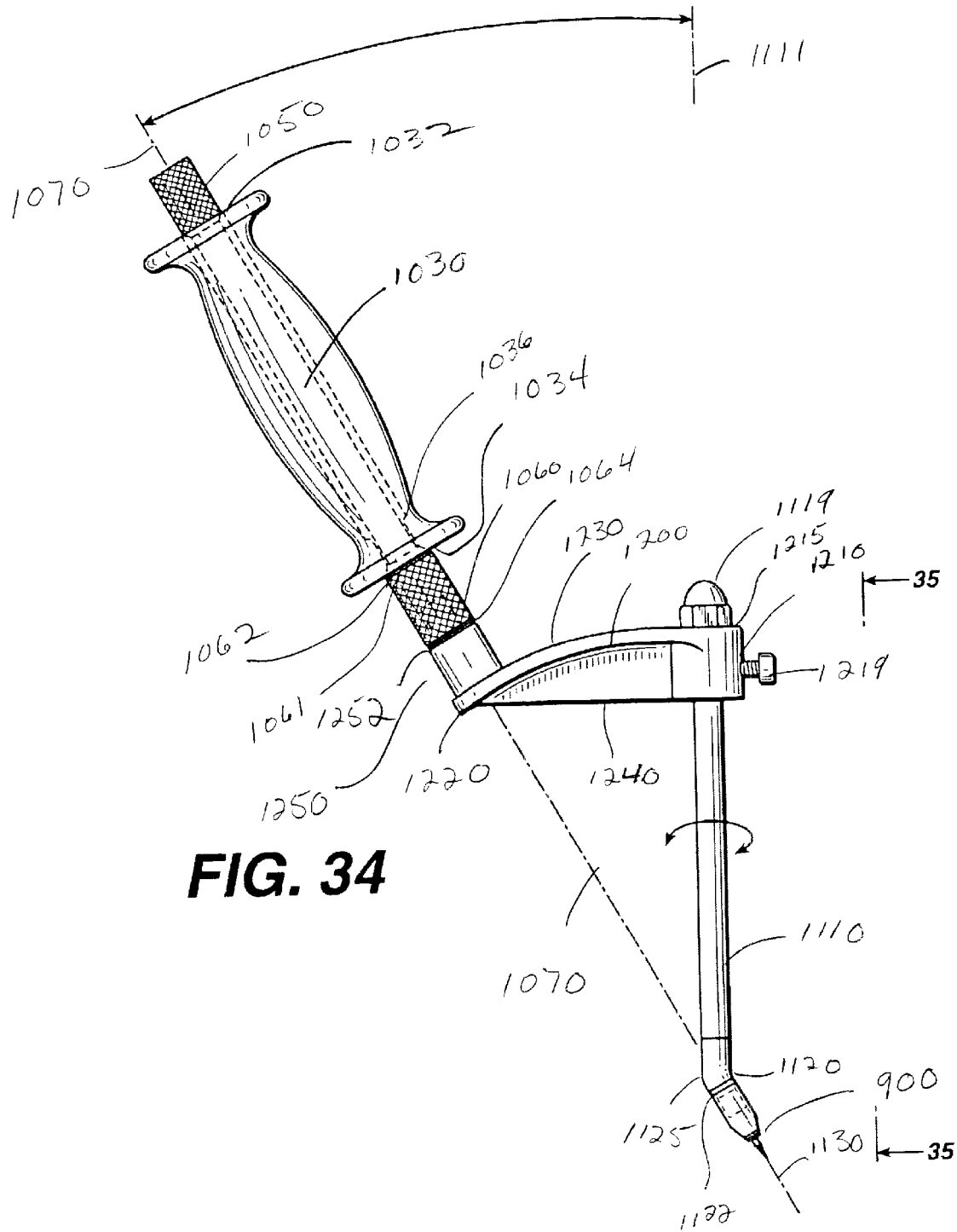
FIG. 34 is a side view of the instrument of FIG. 33.
Figure 35:
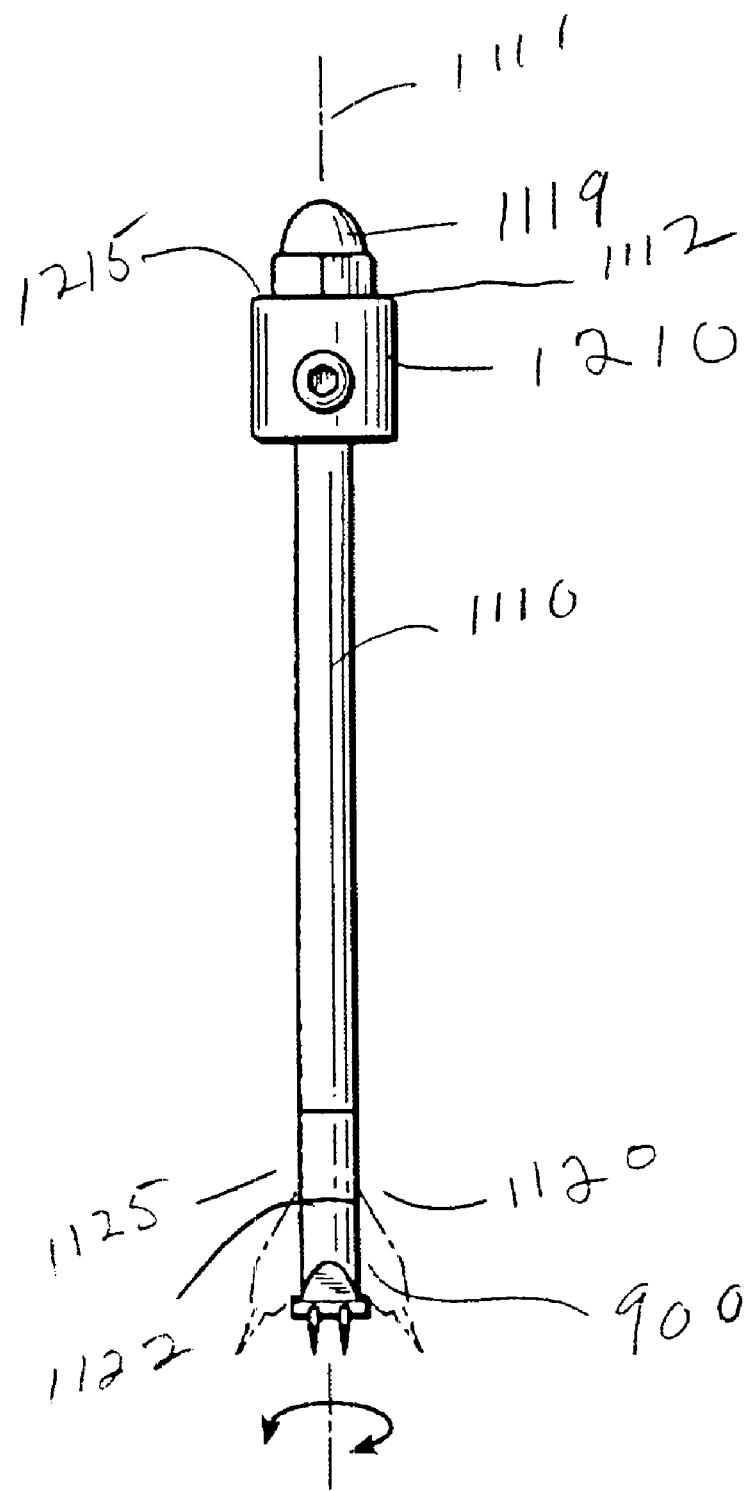
FIG. 35 is a front view of the instrument of FIG. 34.

A novel combination slap-hammer and insertion instrument 1000 useful to mount the fixation devices of the present invention in bone is illustrated in FIG. 33. As seen in FIGS.

Figure 36:
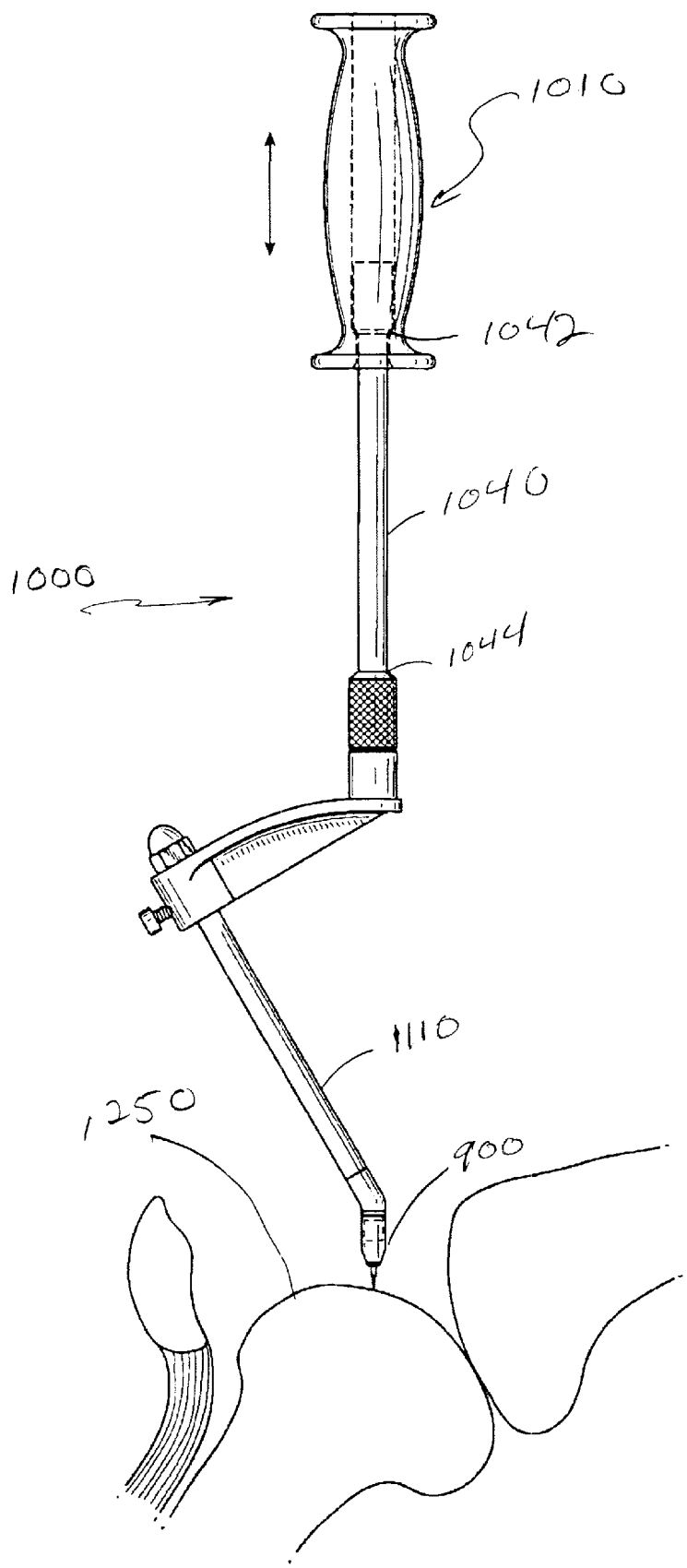
FIG. 36 illustrates a side view of the instrument of FIG. 33 shown engaging the bottom surface of femur.
Figure 37:
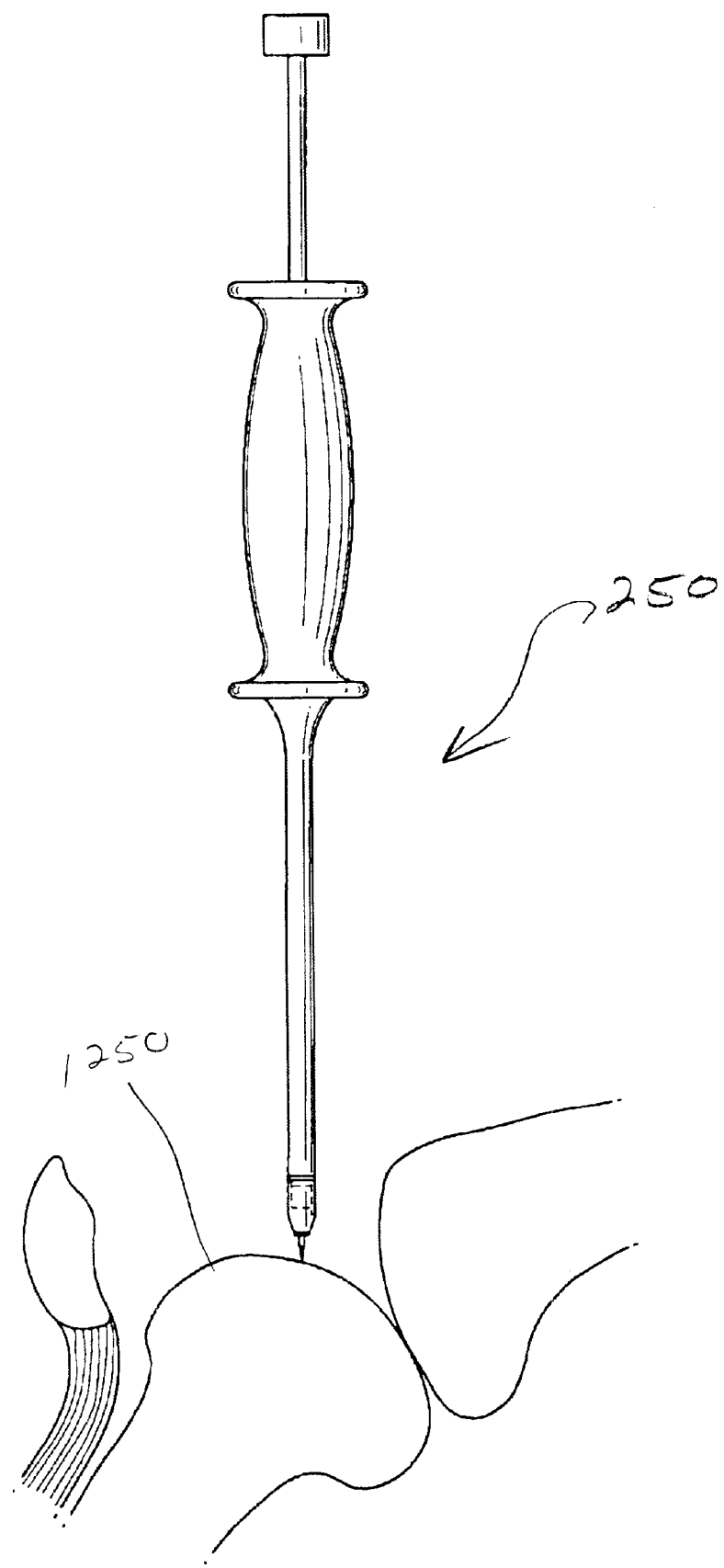
FIG. 37 is a side view illustrating a conventional slap hammer instrument engaging the bottom surface of a femur.

33–36, the instrument 1000 is seen to have a hammer handle 1010 slidably mounted to a hammer slide rod 1040. The hammer handle 1010 is seen to have proximal end 1012 and distal end 1014. The handle is further seen to have curved handle surface 1015 and proximal flange 1017 and distal flange 1019. Adjacent to the proximal flange 1017 is the proximal flange surface 1022, while adjacent to the distal flange 1019 is the distal flange surface 1020. Hammer handle 1010 is seen to have longitudinal passage 1030. The handle 1010 is further seen to have proximal opening 1032, distal opening 1034, both of which communicate with the longitudinal passage 1030. Toward the distal end 1014 of hammer handle 1010, and extending into the longitudinal passage 1030, is the stop shoulder 1036. The handle 1010 is slidably mounted to the hammer slide rod 1040. Slide rod 1040 is seen to have proximal threaded end 1042 and distal threaded end 1044. Mounted to the proximal threaded end 1042 is the proximal knurled nut 1050. Rod 1040 is mounted at the distal threaded end 1044 to the distal knurled coupling 1060 having internal threads 1062. The hammer slide rod 1040 is further seen to have longitudinal axis 1070. The movement of the hammer member 1010 is seen to be constrained or limited along rod 1040 when shoulder 1036 contacts nut 1050 and when distal flange surface 1020 contacts proximal end 1061 of coupling 1060. The instrument 1010 is further seen to have a mounting member 1200 having first end 1210 and second end 1220. The mounting member 1200 is seen to have top curved side 1230 and bottom side 1240. Mounted to the top curved side 1230 adjacent to second end 1220 is the hammer connector 1250. Hammer connector 1250 is a cylindrical member having a threaded end 1252. Threaded end 1252 engages screw threads 1062 in distal end 1064 of coupling member 1060 for mounting the hammer handle 1010 and the hammer slide rod 1040 to the mounting member 1200 in an angulated manner as shown. Adjacent to end 1210 is the mounting rod passage 1215, having proximal end 1216 which extends through mounting member 1200. Extending transversely through end 1210 into the passage 1215 is the transverse threaded screw opening 1217 for receiving retaining screw 1219. Rotatably mounted in the mounting rod passage 1215, is the mounting rod 1110. Mounting rod 1110 is seen to have proximal screw threaded end 1112 and distal end 1120. The diameter of threaded end 1112 is less than the diameter of the rod 1110. Distal end 1120 is seen to have the angulated section 1125. Angulated section 1125 is seen to have longitudinal axis 1130 which is coincident with and/or parallel to longitudinal axis 1070. The mounting rod 1110 is seen to have longitudinal axis 1111. Adjacent to distal end 1120 is the screw threaded mounting section 1122. Disposable end assemblies 800 and 900, as previously described, may be mounted to threaded end 1122. The rod 1110 is maintained is a fixed angular spatial position with respect to the mounting member 1200 by tightening set screw 1219, but is rotatable within the passage 1215 by loosening set screw 1219. Rod 1110 is fixed in place with respect to up and down motion with respect to member 1200 by the mounting top nut 1119 mounted to the proximal end 1112, and by an internal shoulder (not shown) projecting into passage 1215 just distal to proximal end 1216. As seen in FIGS. 36 and 37, the unique angulation provided by the instrument 1000 of the present invention provides the orthopedic surgeon with easier access with minimal incision when either tapping holes into a femur 1250 or inserting fixation devices as described herein. As seen in FIG. 37, when using a conventional slap hammer/insertion device 250 or 400, it is necessary for the orthopedic surgeon to make a more drastic incision and move the patella and the patella tendon more drastically in order to access the interior surfaces on femur 1250, thereby complicating the procedure and possibly causing increased trauma to the patients knee. The unique configuration of instrument 1100 provides for these advantages. The instruments 1100 are used to insert the fixation devices and combinations previously described herein using the procedures as described herein. The degree of angulation of the longitudinal axis 1130 of the angulated section 1125 and the longitudinal axis 1070 hammer slide rod 1040 with respect to longitudinal axis 1111 will be sufficient to provide effective access to the interior of a knee with minimal length incisions and minimal displacement of the parts of the knee. For example, the angle may typically vary from 0 degrees to 50 degrees, more preferably from 20 degrees to 30 degrees.

The fixation devices of the present invention, and the combination of the fixation devices with insertion members, and methods of using such devices and combinations, of the present invention have many advantages. The advantages include providing a fast and routine way to fixate a matrix of tissue engineered tissue or other tissue. The fixation devices and combination, because they eliminate the need for suture knot tying, can be utilized in arthroscopic surgical procedures that require a minimum of surgical incisions and thus greatly reduce patient morbidity. In addition, the fixation devices and combination have been demonstrated to provide excellent matrix fixation without damaging the surrounding normal cartilaginous tissue, unlike the conventional fixation of chondral defect matrices with traditional suture that must be passed through (and thus damage) the surrounding tissue. The instruments of the present invention provide for a reusable section, and a distal disposable section that can be discarded.

Although this invention has been shown and described with respect to detailed embodiments thereof, it will be understood by those skilled in the art that various changes in form and detail may be made without departing from the spirit and scope of the claimed invention.

I claim:

1. An instrument for inserting a graft fixation device into bone, said instrument comprising:
   a mounting member having a first end, an opposed second end, a top and a bottom;
   an elongated slide rod member having a proximal end and a distal end and an outer surface and a longitudinal axis, wherein the distal end of the slide rod is mounted to the first end of the mounting member such that the longitudinal axis of the slide rod is angulated at an acute angle with respect to the mounting member;
   a hammer handle member having a distal end, a proximal end, an outer surface, a first flange member extending from the proximal end, a second flange member extending from the distal end, an inner passage therethrough and a longitudinal axis, wherein the hammer handle is slidably mounted to the slide rod member;
   a mounting rod having a proximal end and an angulated distal end, wherein the angulated distal end has a longitudinal axis, wherein the proximal end of the mounting rod is mounted to the second end of the mounting member; and,
   a pair of spaced apart prongs extending longitudinally from the distal end of the mounting rod,
   wherein the longitudinal axis of the slide rod is parallel to the longitudinal axis of the angulated distal end of the mounting rod.

2. The instrument of claim 1 further comprising an inner shoulder extending into the inner passage of the hammer handle.

3. The instrument of claim 1, wherein the mounting rod additionally comprises a screw threaded distal end, and a housing having an inner cavity and inner screw threads mounted to said threaded distal end, and the prongs extend out from said housing.

4. The instrument of claim 1 wherein the mounting rod is rotatably mounted to the mounting member.

5. The instrument of claim 1 wherein the mounting member has a threaded member mounted thereto at an angle for engaging a first end of a threaded coupling member, and wherein the distal end of the slide member is threaded and engages a second end of the coupling member.

6. The instrument of claim 1 wherein the longitudinal axis of the slide rod is coincident with the longitudinal axis of the angulated distal end.

* * * * *